United States Patent
Kojima et al.

(10) Patent No.: US 8,235,914 B2
(45) Date of Patent: Aug. 7, 2012

(54) MEASURING DEVICE FOR A LANCET-INTEGRATED SENSOR

(75) Inventors: Shinichi Kojima, Matsuyama (JP); Yoshinobu Tokuno, Ehime (JP)

(73) Assignee: Panasonic Corporation, Osaka (JP)

( * ) Notice: Subject to any disclaimer, the term of this patent is extended or adjusted under 35 U.S.C. 154(b) by 439 days.

(21) Appl. No.: 12/267,161

(22) Filed: Nov. 7, 2008

(65) Prior Publication Data

US 2009/0069719 A1 Mar. 12, 2009

Related U.S. Application Data

(62) Division of application No. 10/222,000, filed as application No. PCT/JP02/00386 on Jan. 21, 2002, now Pat. No. 7,691,071.

(30) Foreign Application Priority Data

Jan. 19, 2001 (JP) .................................. 2001-11275

(51) Int. Cl.
- *A61B 5/00* (2006.01)
- *A61B 17/14* (2006.01)
- *A61B 17/32* (2006.01)
- *B65D 81/00* (2006.01)

(52) U.S. Cl. ......... 600/583; 600/573; 600/584; 606/181

(58) Field of Classification Search .................. 600/583, 600/576, 347, 365; 606/167, 181, 182, 185; 604/6.15, 6.16, 117, 136

See application file for complete search history.

(56) References Cited

U.S. PATENT DOCUMENTS

| | | | |
|---|---|---|---|
| 4,627,445 A | 12/1986 | Garcia et al. | |
| 4,637,403 A | 1/1987 | Garcia et al. | |
| 4,873,993 A | 10/1989 | Meserol et al. | |
| 5,279,294 A | 1/1994 | Anderson et al. | |
| 5,385,571 A | 1/1995 | Morita | |
| 5,554,166 A | 9/1996 | Lange et al. | |
| 5,613,978 A | 3/1997 | Harding | |
| 5,776,078 A | 7/1998 | Wardlaw | |
| 5,971,941 A | 10/1999 | Simons et al. | |
| 6,036,924 A * | 3/2000 | Simons et al. | 422/100 |
| 6,051,392 A | 4/2000 | Ikeda et al. | |
| 6,071,294 A | 6/2000 | Simons et al. | |
| 6,561,989 B2 | 5/2003 | Whitson | |
| 6,706,159 B2 | 3/2004 | Moerman et al. | |

FOREIGN PATENT DOCUMENTS

| | | |
|---|---|---|
| EP | 0 449 525 A1 | 10/1991 |
| EP | 0 589 186 | 3/1994 |
| EP | 0 848 933 A1 | 6/1998 |

(Continued)

OTHER PUBLICATIONS

Supplementary European Search Report issued Nov. 25, 2008 in European Application No. 02 71 0317.

(Continued)

*Primary Examiner* — Jeffrey G Hoekstra

(74) *Attorney, Agent, or Firm* — Wenderoth, Lind & Ponack, L.L.P.

(57) ABSTRACT

A sensor and a lancet are integrated with each other. A thin strip-shaped sensor and a lancet are integrated so that the lancet moves in parallel, along a longitudinal direction of the sensor. A measuring device to which an integrated lancet and sensor is attached is provided with a function of driving the attached lancet.

19 Claims, 20 Drawing Sheets

FOREIGN PATENT DOCUMENTS

| | | |
|---|---|---|
| EP | 0 569 124 B1 | 5/2000 |
| EP | 1 031 319 A1 | 8/2000 |
| EP | 1 609 416 A2 | 12/2005 |
| EP | 0 931 507 B1 | 7/2006 |
| JP | 3-37935 | 6/1991 |
| JP | 5-285127 | 11/1993 |
| JP | 5-88503 | 12/1993 |
| JP | 6-7329 | 1/1994 |
| JP | 6-78903 | 3/1994 |
| JP | 6-28729 | 4/1994 |
| JP | 6-237922 | 8/1994 |
| JP | 6-339473 | 12/1994 |
| JP | 7-16218 | 1/1995 |
| JP | 8-258860 | 10/1996 |
| JP | 9-89885 | 4/1997 |
| JP | 9-266898 | 10/1997 |
| JP | 2561697 | 10/1997 |
| JP | 9-294737 | 11/1997 |
| JP | 10-28683 | 2/1998 |
| JP | 10-101165 | 4/1998 |
| JP | 10-508527 | 8/1998 |
| JP | 11-206742 | 8/1999 |
| JP | 11-236086 | 8/1999 |
| JP | 2000-231 | 1/2000 |
| JP | 2000-14662 | 1/2000 |
| JP | 2000-217804 | 8/2000 |
| JP | 2000-225110 | 8/2000 |
| JP | 2000-232973 | 8/2000 |
| JP | 2000-245717 | 9/2000 |
| JP | 2000-262498 | 9/2000 |
| JP | 2000-296896 | 10/2000 |

OTHER PUBLICATIONS

Japanese Abstract for Japanese Application No. 2000-185034.
International Search Report issued May 14, 2002 in International Application No. PCT/JP02/00386.
Chinese Office Action issued Dec. 3, 2004 in Chinese Application No. 02800136.2.
Office Action issued Nov. 4, 2009 in U.S. Appl. No. 12/267,009.
Office Action issued Jun. 2, 2009 in U.S. Appl. No. 12/267,122.

* cited by examiner

Fig.23 (a)
(PRIOR ART)
Fig.23 (b)
(PRIOR ART)
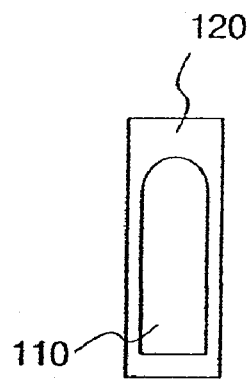
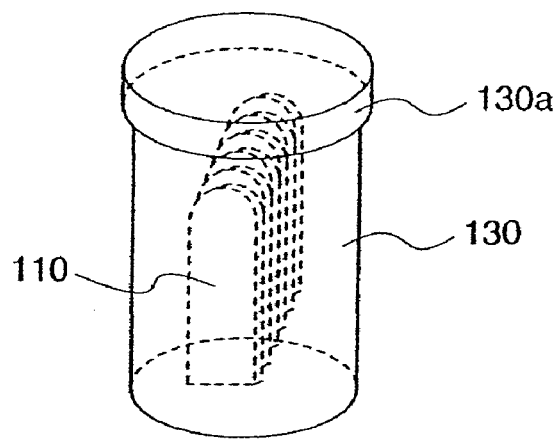
Fig.24
(PRIOR ART)
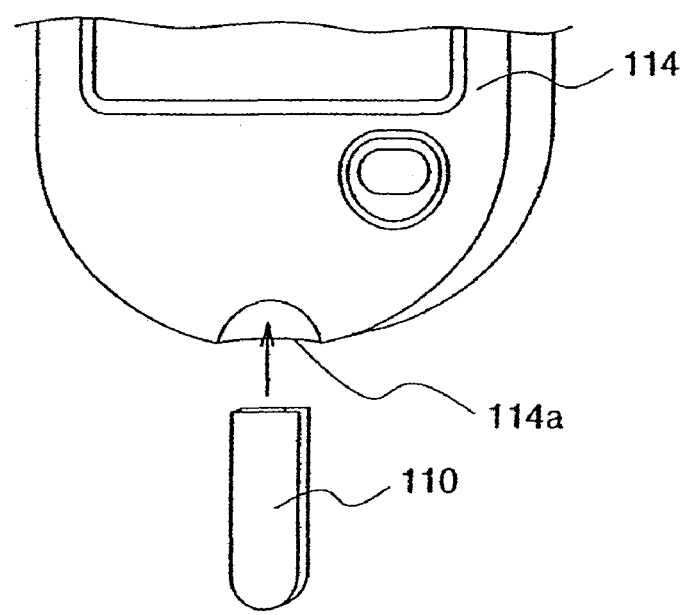

MEASURING DEVICE FOR A LANCET-INTEGRATED SENSOR

This is a divisional application of U.S. patent application Ser. No. 10/222,000 filed Nov. 26, 2002, now U.S. Pat. No. 7,691,071, which is the National Stage of International Application No. PCT/JP02/00386, filed Jan. 21, 2002.

TECHNICAL FIELD

The present invention relates to a lancet-integrated sensor for extracting bodily fluid of a man or an animal, and easily analyzing characteristics of the bodily fluid and, more particularly, to an improved lancet-integrated sensor that is characterized by a construction in which a lancet for lancing skin to extract bodily fluid is integrated with a sensor for collecting the bodily fluid extracted at a surface of the skin to analyze the fluid.

Further, the present invention relates to a measuring device for measuring components of bodily fluid such as blood sugar and, more particularly, to an improved measuring device for a lancet-integrated sensor.

Furthermore, the present invention relates to an improved cartridge for housing biosensors of this type.

BACKGROUND ART

Conventionally, as a device for easily analyzing characteristics of bodily fluid of a man or an animal, for example, a device for electrochemically measuring blood sugar has already been put to practical use.

A biosensor is a device of this type, and hereinafter, a biosensor and a measuring device to be combined with the biosensor will be described.

FIG. 21 shows a long and narrow strip-shaped sensor 31 for collecting blood, which is set in a sensor insertion slot 31a of a measuring device 32. The sensor 31 is provided with a cavity (not shown) for collecting blood, in its semi-circular front end that protrudes from the measuring device 32 in a state where the sensor 31 is housed in the measuring device 32. Further, the sensor 31 is provided with, in the cavity, a reagent layer containing an enzyme, an electron carrier, and the like, and electrodes.

The measuring device 32 contains an electric circuit for measuring a current value according to concentration of glucose in blood, which current is generated by a reaction between the glucose in blood and the reagent layer, by applying a voltage to the electrode, and measured blood sugar is displayed on a display 33 which is placed on an upper surface of the measuring device 32.

For every measurement, a new sensor 31 is inserted into the sensor insertion slot on a side surface of the measuring device 32, and blood of a patient is applied onto the sensor 31 to perform measurement. The sensor 31 after measurement is discarded for hygienic reasons.

Usually, skin of a body part, such as a fingertip, is lanced with a lancet device 34 as shown in FIG. 22(a) to extract a very small quantity of blood, and the blood is collected in the cavity of the sensor 31.

In the lancet device 34 whose internal structure is shown in FIG. 22(b), a force is elastically applied to a lancet 35 by a spring coil 36. When an operation button 37 is pushed, an engagement member 37a which is united with the operation button 37 is disengaged from a ring-shaped groove 35a of the lancet 35, whereby a force applied to the lancet 35 by the spring 36 is released, and a tip of a needle 35b of the lancet 35 forcibly projects from a front end of an approximately cylindrical-shaped case 38. The lancet 35 comprises the needle 35b which is made of metal, and a holder 35c for holding the needle 35b, which is made of plastic. Usually, the lancet 35 is replaced with a new one at every measurement, for hygienic reasons.

Further, a biosensor to be used for analyzing bodily fluid extracted from a man or an animal is usually preserved in a state where it is wrapped with an aluminum wrapper or the like, or in a state where it is contained in a plastic case. When the biosensor is used, it is taken out of the aluminum wrapper or the plastic case.

FIG. 23(a) is a diagram illustrating a state where a biosensor 110 having a reagent layer (not shown) for analyzing bodily fluid, and an electrode (not shown) for removing an electric signal according to result of analysis, is hermetically wrapped with an aluminum wrapper 120. To be specific, a biosensor 110 which comprises an approximately rectangular-shaped plate member having a shorter side of an approximately semi-circular shape is wrapped with an aluminum wrapper 120 having a rectangular shape that is a little larger than the biosensor 110. FIG. 23(b) shows a state where a plurality of biosensors 110, which are arranged with their approximately-semi-circular-shaped ends facing upward and their surfaces being in contact with each other, are hermetically contained in a cylindrical plastic case 130 with a lid.

When performing measurement, the biosensor 110 which is preserved as shown in FIG. 23(a) or 23(b) is removed, and another shorter side of the biosensor 110, which is not the approximately-semi-circular-shaped side, is inserted into a biosensor insertion slot 114a of a measuring device 114 to prepare for measurement as shown in FIG. 24.

Since the conventional biosensor and measuring device thereof are constructed as described above, when preparing for measurement, a patient sets a new lancet 35 in the lancet device 34 as described above. Then, the patient sets a new sensor 31 in the measuring device 32, whereby preparation for measurement is completed. Thereafter, the patient operates the lancet device 34 to take blood from his/her fingertip or the like, and applies it onto a front end of the sensor 31 that is set in the measuring device 32 to perform measurement. In this way, the patient must perform replacement of the lancet and replacement of the sensor separately for every measurement, resulting in complicated operation.

Further, since it is necessary to monitor blood sugar a few times a day, sizes of these devices are reduced in consideration of portability. In a conventional system, however, the patient must carry the sensor 31, the measuring device 32, the lancet 35, and the lancet device 34 together, resulting in a voluminous system as a whole. Further, since the patient must manage the sensor 31 and the lancet 35 separately, operation and measurement are troublesome, resulting in poor usability.

The present invention is made to solve the above-mentioned problems and has for its object to provide a lancet-integrated sensor in which a sensor and a lancet are integrated to facilitate operation and management, and improve portability, as well as a measuring device to be combined with the lancet-integrated sensor.

Further, with respect to the conventional biosensors, as described above, each biosensor is wrapped with an aluminum wrapper, or plural biosensors are stored in a plastic case with a lid, whereby the biosensors are prevented from contamination due to moisture.

However, when preparing for measurement, a patient must break the aluminum wrapper 120 to take the biosensor 110, or open the lid 130a of the plastic case 130 to take the biosensors 110 one by one. Further, the patient must insert this taken biosensor 110 toward the sensor insertion slot 114a of the measuring device 114. Therefore, preparation for measurement is troublesome, and usability is poor.

The present invention is made to solve the above-mentioned problems and has for its object to provide a biosensor cartridge by which a biosensor stored in a case is easily inserted into a measuring device without troublesome operation.

SUMMARY OF THE INVENTION

To be specific, in order to solve the above-mentioned conventional problems, a lancet-integrated sensor according to a first aspect of the present invention is constituted by integrating a lancet for lancing skin of a subject to extract its bodily fluid, and a sensor body for analyzing this extracted bodily fluid. The sensor body has a shape of a long and narrow strip; and the lancet is driven along a longitudinal direction of the sensor body by an external driving device, thereby lancing the skin.

Accordingly, the sensor and the lancet are integrated with each other, whereby the sensor and the lancet can be managed not separately but together, resulting in easy handling. When measuring bodily fluid, since the sensor and the lancet can be set as a single unit on a measuring device, operability is improved. Further, the lancet-integrated sensor is convenient to carry about. Furthermore, since the lancet is movable along the longitudinal direction of the long and narrow strip-shaped sensor, a size of the lancet-integrated sensor is reduced, resulting in easy handling.

Further, according to a second aspect of the present invention, in the lancet-integrated sensor defined in accordance with the first aspect, the sensor body has an internal space through which the lancet can pass, and holds the lancet in the space.

Accordingly, the lancet is held in the sensor, thereby providing a specific construction for further reducing the size of the lancet-integrated sensor.

Further, according to a third aspect of the present invention, in the lancet-integrated sensor defined in accordance with the second aspect, a long and narrow space for housing the lancet is formed in the sensor body.

Accordingly, the long and narrow space facilitates positioning of the lancet and the sensor, whereby a space for attachment of the sensor and the lancet, and a space for moving the lancet can be secured.

Further, according to a fourth aspect of the present invention, in the lancet-integrated sensor defined in accordance with any of the first to third aspects, the sensor body is obtained by bonding two thin plates together, and at least one of the two plates has a concave portion, with the lancet being stored in a space which is formed by the concave portion of the two plates bonded together.

Accordingly, a thinner lancet-integrated sensor can be provided.

Further, according to a fifth aspect of the present invention, in the lancet-integrated sensor defined in accordance with any of the first to fourth aspects, when the lancet lances the skin to extract the bodily fluid, the lancet projects its needle tip from an inside of the sensor body in which the lancet is stored.

Accordingly, the needle tip of the lancet is housed in the sensor, whereby safety is further improved.

Further, according to a sixth aspect of the present invention, in the lancet-integrated sensor defined in accordance with any of the first to fifth aspects, a cavity for collecting the bodily fluid is provided separately from the space in the sensor body where the lancet is housed.

Accordingly, risk of damaging an inside of the cavity for collecting the bodily fluid by the lancet is avoided.

Further, according to a seventh aspect of the present invention, in the lancet-integrated sensor defined in accordance with any of the first to sixth aspects, the space in the sensor body for housing the lancet also serves as a cavity for collecting the bodily fluid, and the bodily fluid is collected into the space for housing the lancet.

Accordingly, the bodily fluid is collected into the space where the lancet moves to lance the skin, whereby the size of the lancet-integrated sensor is further reduced.

Further, according to an eighth aspect of the present invention, in the lancet-integrated sensor defined in accordance with any of the first to sixth aspects, an inlet of a cavity for collecting the bodily fluid is provided at an end of the sensor from which the needle tip of the lancet is projected.

Accordingly, the bodily fluid is stored in the cavity at a front end of the sensor from which the needle tip protrudes, whereby time during which collected bodily fluid is exposed to air is minimized.

Further, according to a ninth aspect of the present invention, in the lancet-integrated sensor defined in accordance with any of the first to eighth aspects, the sensor body has, in a cavity, an electrode for outputting an analysis result of characteristics of the bodily fluid.

Accordingly, the characteristics of the bodily fluid can be electrically measured.

Further, according to a tenth aspect of the present invention, in the lancet-integrated sensor defined in accordance with the ninth aspect, a connection terminal to be connected with an external measuring device to electrically measure the characteristics of the bodily fluid is provided at an end of the sensor body having the cavity.

Accordingly, the characteristics of the bodily fluid can be electrically measured by the external measuring device that is connected to the sensor.

Further, according to an eleventh aspect of the present invention, in the lancet-integrated sensor defined in accordance with any of the first to tenth aspects, a reagent that reacts with the collected bodily fluid is provided in the cavity.

Accordingly, the characteristics of the bodily fluid can be optically or electrochemically measured by a chemical reaction between the reagent and the bodily fluid.

Further, according to a twelfth aspect of the present invention, in the lancet-integrated sensor defined in accordance with any of the first to tenth aspects, an end of the lancet on a side opposite to the needle tip projects from the sensor body, and a projecting end is engaged with a driving device of the external measuring device, whereby the lancet is driven to perform a skin lancing operation.

Accordingly, the external driving device for driving the lancet can hold a base end of the lancet, and drive the lancet in the longitudinal direction of the sensor to make the lancet perform the lancing operation.

Further, according to a thirteenth aspect of the present invention, in the lancet-integrated sensor defined in accordance with the twelfth aspect, a connector to be engaged with the driving device of the external measuring device is provided at the end of the lancet on the opposite side to the needle tip, and the connector is engaged with the driving device, whereby the lancet performs the skin lancing operation.

Accordingly, the external driving device for driving the lancet can easily hold the base end of the lancet to drive the lancet more reliably.

Further, according to a fourteenth aspect of the present invention, in the lancet-integrated sensor defined in accordance with the thirteenth aspect, the connector is made of a resin, and has a diameter larger than that of the lancet.

Accordingly, the external driving device for driving the lancet can easily hold the base end of the lancet to drive the lancet more reliably.

Further, according to a fifteenth aspect of the present invention, in the lancet-integrated sensor defined in accordance with any of the first to fourteenth aspects, a detachable protection cover is fitted to the needle tip of the lancet, and the protection cover is removed during the skin lancing operation performed by the lancet.

Accordingly, injury by the needle tip of the lancet, and contamination of the needle tip are avoided.

Further, according to a sixteenth aspect of the present invention, in the lancet-integrated sensor defined in accordance with the fifteenth aspect, the protection cover has a tube part for housing the needle tip therein, and a wide grip part for facilitating removal of the protection cover from the lancet, which grip part is provided on the needle tip side of the tube part.

Accordingly, removal of the protection cover that covers the needle tip of the lancet is facilitated.

Further, according to a seventeenth aspect of the present invention, in the lancet-integrated sensor defined in accordance with the fifteenth aspect, engagement of the lancet and the driving device, and attachment of the sensor body integrated with the lancet to the measuring device are performed with holding of the grip part of the protection cover.

Accordingly, a user can attach the sensor and the lancet to the measuring device by griping the protection cover, without holding the sensor and the lancet.

Further, according to an eighteenth aspect of the present invention, in the lancet-integrated sensor defined in accordance with the sixteenth aspect, a space in which the front end of the sensor body can be housed is formed in the tube part.

Accordingly, the sensor, which is fitted to the external measuring device and has finished measurement, can be set so that its front end is housed in the protection cover. Then, this used sensor in this state can be removed from the measuring device to be hygienically disposed of.

Further, according to a nineteenth aspect of the present invention, the lancet-integrated sensor defined in accordance with any of the first to eighteenth aspects is provided with a holder which covers a periphery of the integrated sensor body and lancet to hold these members.

Accordingly, a periphery of the integrated sensor and lancet is covered with the holder, and the user can easily handle the lancet-integrated sensor by griping the holder.

Further, according to a twentieth aspect of the present invention, in the lancet-integrated sensor defined in accordance with the nineteenth aspect, the holder is made of a transparent material.

Accordingly, the sensor and the lancet in the holder can be easily checked, whereby handling is further facilitated.

Further, according to a twenty-first aspect of the present invention, the lancet-integrated sensor defined in accordance with any of the first to twentieth aspects is of a disposable type, which will be discarded after performing collection and analysis of bodily fluid one time.

Accordingly, not only the sensor but also the lancet are necessarily renewed for every measurement, such that these devices can be hygienically managed.

Further, according to a twenty-second aspect of the present invention, there is provided a measuring device to which a lancet-integrated sensor that is constituted by integrating a lancet for lancing skin of a subject to extract its bodily fluid, and a sensor body for analyzing this extracted bodily fluid, are detachably attached, for measuring characteristics of the bodily fluid collected by the lancet-integrated sensor, and the measuring device includes a lancet driving device for driving, after the lancet-integrated sensor is attached to the measuring device, the lancet so as to lance the skin.

Accordingly, a conventional lancet device is integrated with the measuring device, whereby a lancing operation and measurement can be performed by the measuring device alone without requiring a separate lancet device as is conventional. Further, since the lancet integrated with the sensor is attached to the measuring device for every measurement, only the lancet driving device is to be added to the conventional measuring device and, therefore, the measuring device can be realized at low cost.

Further, according to a twenty-third aspect of the present invention, in the measuring device defined in accordance with the twenty-second aspect, at least one end of the lancet-integrated sensor is projected from the measuring device when attachment of the lancet-integrated sensor to the measuring device is completed.

Accordingly, a patient lances his/her fingertip with the lancet, and drops bodily fluid onto the sensor, with an exposed end of the lancet-integrated sensor as a mark, whereby an operation is facilitated. Further, since an end of the lancet-integrated sensor is exposed, the measuring device is prevented from being contaminated with the bodily fluid or the like.

Further, according to a twenty-fourth aspect of the present invention, in the measuring device defined in accordance with the twenty-second or twenty-third aspects, the lancet driving device drives the lancet of the lancet-integrated sensor so that a needle tip of the lancet is projected from the sensor only when it lances the skin to collect the bodily fluid and, at all other times, the needle tip is housed in the sensor.

Accordingly, the needle tip of the lancet is housed in the sensor, whereby safety is further improved.

Further, according to a twenty-fifth aspect of the present invention, the measuring device defined in accordance with the twenty-fourth aspect is provided with a connector for maintaining electrical connection with an electrode terminal that is placed at an end of the sensor body of the lancet-integrated sensor, to measure characteristics of collected bodily fluid by an internal electric circuit.

Accordingly, the characteristics of the bodily fluid can be electrically measured.

Further, according to a twenty-sixth aspect of the present invention, in the measuring device defined in accordance with any of the twenty-second to twenty-fifth aspects, the lancet driving device drives the lancet when it is engaged with an end of the lancet on a side opposite to the needle tip, or when a grip part of a protection cover is gripped.

Accordingly, the external driving device for driving the lancet holds the end of the lancet, and drives the lancet in a longitudinal direction of the sensor to make the lancet perform a lancing operation. Further, when a holding part is provided on the end of the lancet, the driving device can easily hold the lancet.

Further, according to a twenty-seventh aspect of the present invention, in the measuring device defined in accordance with the twenty-sixth aspect, the lancet driving device has a spring for applying a force to the lancet in the longitudinal direction of the sensor, and the force of the spring is released by a press button that is provided on the measuring device to project the lancet.

Accordingly, an end of the lancet or the holding part is engaged with an end of the spring, whereby elasticity of this coil spring is applied to the lancet.

Further, according to a twenty-eighth aspect of the present invention, in the measuring device defined in accordance with any of the twenty-first to twenty-seventh aspects, a lancet-integrated sensor as defined in accordance with any of the fifteenth to eighteenth aspects is detachably attached to the measuring device; attachment of the lancet-integrated sensor to the measuring device is performed with the tip of the lancet being covered with a protection cover, the sensor is held by the connector of the measuring device, and an end of the lancet on the side opposite to the needle tip is supported by the lancet driving device.

Accordingly, injury by the needle tip of the lancet, and contamination of the needle tip are avoided.

Further, according to a twenty-ninth aspect of the present invention, in the measuring device defined in accordance with any of the twenty-second to twenty-eighth aspects, a lancet-integrated sensor as defined in accordance with any of the nineteenth to twentieth aspects is detachably attached to the measuring device, the sensor is held by the connector, and an end of the lancet on the side opposite to the needle tip or the grip part of the protection cover is held by the driving device, in accordance with operation of engaging the holder with the measuring device, so that the sensor and the lancet are attached to the measuring device in a state where the sensor and the lancet are being held by the holder.

Accordingly, a periphery of the integrated sensor and lancet is covered with the holder, and the user can easily handle the lancet-integrated sensor by gripping the holder.

Further, according to a thirtieth aspect of the present invention, in the measuring device defined in accordance with any of the twenty-second to twenty-ninth aspects, a lancet-integrated sensor which has been used is ejected from the measuring device body without being touched by hands, by operating an operation button that is provided on the measuring device body.

Accordingly, the user can remove a used lancet-integrated sensor from the measuring device without touching it so that his/her hands are not contaminated, whereby infectious diseases or the like are avoided.

Further, according to a thirty-first aspect of the present invention, in the measuring device defined in accordance with any of the twenty-second to thirtieth aspects, an amount of projection of the needle tip of the lancet from the front end of the sensor is displayed on a display device that is provided on the measuring device body.

Accordingly, the user can certainly confirm the amount of projection of the needle tip of the lancet with the display device, whereby usability is improved.

Further, according to a thirty-second aspect of the present invention, there is provided a lancet-integrated sensor which is constituted by integrating a lancet having a needle for lancing skin to collect bodily fluid, and a sensor for analyzing this collected bodily fluid, wherein a cavity for slidably housing a part of the lancet is formed in the sensor, and a force is applied to the lancet in a direction opposite to a direction along which the needle lances the skin, to house the needle in the sensor, whereby the lancet and the sensor are locked with each other.

Accordingly, the lancet onto which bodily fluid sticks is locked in the sensor, whereby a user can safely remove the lancet-integrated sensor from the measuring device without touching the needle by mistake.

Further, according to a thirty-third aspect of the present invention, in the lancet-integrated sensor defined in accordance with the thirty-second aspect: the lancet comprises an approximately-rectangular-shaped plate member; the needle of the lancet is arranged in the vicinity of a center of one of shorter sides of the plate member so that it projects along a longitudinal direction of the plate member; the cavity is formed in a shape approximately identical to an outline shape that is obtained when the lancet is slid by a predetermined amount along the longitudinal direction thereof; and openings for projecting the needle and another side of the lancet to the outside of the sensor are formed at a front end and a rear end of the sensor, respectively.

Accordingly, the lancet onto which the bodily fluid sticks is locked in the sensor, whereby the user can safely remove the lancet-integrated sensor from the measuring device without touching the needle tip by mistake.

Further, according to a thirty-fourth aspect of the present invention, in the lancet-integrated sensor defined in accordance with the thirty-second or thirty-third aspects: either a convex portion for locking or a concave portion for locking is formed on the lancet, and either a concave portion for locking or a convex portion for locking which is engaged with the convex portion or the concave portion of the lancet is formed on the sensor; and the lancet and the sensor are locked with each other when the convex portion for locking and the concave portion for locking are engaged with each other.

Accordingly, the lancet onto which the bodily fluid sticks is locked in the sensor, whereby the user can safely remove the lancet-integrated sensor from the measuring device without touching the needle tip by mistake.

Further, according to a thirty-fifth aspect of the present invention, in the lancet-integrated sensor defined in accordance with the thirty-fourth aspect: the lancet has two plate-shaped projections which project from two longer sides of the lancet in a width direction; the projections have the concave portions for locking on their upper surfaces; a cavity for slidably housing the lancet, which is formed in the sensor, has two depressions for housing the two projections of the lancet, which depressions project in a width direction of the cavity; and the depressions have the concave portions for locking at their ceilings.

Accordingly, the lancet onto which the bodily fluid sticks is locked in the sensor, whereby the user can safely remove the lancet-integrated sensor from the measuring device without touching the needle tip by mistake.

Further, according to a thirty-sixth aspect of the present invention, the measuring device for performing measurement using a lancet-integrated sensor, which is defined in accordance with the thirty-third aspect, comprises: a guide member for guiding the lancet-integrated sensor that is inserted from an opening provided on a side surface of the measuring device, thereby restricting a direction along which the lancet-integrated sensor travels in the measuring device; a lancet pressing member which is pushed by a spring member in the measuring device in a direction opposite to the direction along which the lancet-integrated sensor is inserted, and is engaged with another shorter side of the lancet that is guided toward the inside of the measuring device by the guide member, thereby pressing the lancet toward the opening; a locking member for fixing the lancet pressing member at a predetermined position in the measuring device when the lancet-integrated sensor is inserted deeper into the measuring device; an unlocking member for releasing fixation of the lancet pressing member by the locking member, with manual operation; and an ejection member for applying a force to the sensor of the lancet-integrated sensor to push the sensor toward an opening side, with manual operation, which ejection member is provided between the lancet pressing member and the guide member.

Accordingly, it is possible to realize a measuring device which can perform measurement using a lancet-integrated sensor that can be safely removed from the measuring device because the lancet to which the bodily fluid sticks is locked in the sensor to prevent hands of the user from touching the needle tip by mistake and, after measurement, the lancet-integrated sensor can be safely removed from the measuring device with the needle tip being housed in the sensor.

Further, according to a thirty-seventh aspect of the present invention, in the measuring device for a lancet-integrated sensor which is defined in accordance with the thirty-sixth aspect, the ejection member slides an operation lever that is exposed at a main surface of the measuring device, toward the opening side, whereby a pressing member that is united with the operation lever presses the vicinity of both sides of an end of the lancet-integrated sensor, which end is opposite to the side where the lancet lances the skin, thereby ejecting the lancet-integrated sensor.

Accordingly, it is possible to realize a measuring device which can perform measurement using a lancet-integrated sensor that can be safely removed from the measuring device because the lancet to which the bodily fluid sticks is locked in the sensor to prevent hands of the user from touching the needle tip by mistake and, after the measurement, the lancet-integrated sensor can be safely removed from the measuring device with the needle tip being housed in the sensor.

Further, according to a thirty-eighth aspect of the present invention, there is provided a measuring device for performing measurement using a lancet-integrated sensor which is constituted by integrating a lancet for lancing skin to collect bodily fluid, and a sensor for analyzing this collected bodily fluid, wherein: the measuring device for the lancet-integrated sensor has an opening on a side surface; the measuring device has a cavity in which the lancet-integrated sensor can be housed, which cavity is formed corresponding to the opening; a holder attachment part is formed on a side of the measuring device having the opening, which holder attachment part detachably attaches a holder body in which the lancet-integrated sensor can pass through, to the measuring device; and the holder body guides the lancet-integrated sensor when the lancet-integrated sensor is housed in the cavity and, after it is housed in the cavity, the holder body holds a portion of the lancet-integrated sensor in the vicinity of the end where the lancet lances the skin.

Accordingly, the holder body is constituted to be detachable from the measuring device so that replacement or washing of the holder body is easily performed, and the measuring device can be used not only by a specific user but also by other persons, whereby the measuring device for the lancet-integrated sensor can be safely and hygienically used.

Further, according to a thirty-ninth aspect of the present invention, in the measuring device for a lancet-integrated sensor which is defined in accordance with the thirty-eighth aspect: engagement portions of the holder and the holder attachment part have asymmetrical shapes in a vertical direction or in a horizontal direction; and attachment of the holder to the holder attachment part is possible only when the vertical direction of the holder with respect to the holder attachment part is a predetermined direction.

Accordingly, the holder body can always be inserted into the measuring device in a normal direction, and the lancet-integrated sensor is prevented from being inserted upside down into the measuring device.

Further, according to a fortieth aspect of the present invention, in the measuring device for a lancet-integrated sensor which is defined in accordance with the thirty-eighth aspect, the opening of the holder attachment part into which the holder body is inserted has a shape of an approximate rectangle that is side-to-side long, with portions corresponding to corners of the rectangle being rounded, and the opening has smaller openings overhanging in a width direction in the vicinities of centers of two sides in a longitudinal direction.

Accordingly, the opening of the holder attachment part becomes asymmetrical in the longitudinal direction and in the width direction, whereby the holder is prevented from being inserted in a wrong direction.

Further, according to a forty-first aspect of the present invention, in the measuring device for a lancet-integrated sensor which is defined in accordance with the fortieth aspect: the holder body has hinge-shaped stoppers; inner sides of the hinge-shaped stoppers are fixed to the holder body; and outer sides of the hinge-shaped stoppers are engaged with the engagement portions of the holder attachment part.

Accordingly, the holder body can always be inserted into the measuring device in the normal direction, and the lancet-integrated sensor is prevented from being inserted upside down into the measuring device.

Further, according to a forty-second aspect of the present invention, in the measuring device for a lancet-integrated sensor which is defined in accordance with the fortieth aspect: the holder body has a peripheral edge part that extends along a surface of the opening at a periphery of the opening excluding the smaller openings, on the side where the holder body is attached to the measuring device; the hinge-shaped stoppers are provided in portions of the peripheral edge part corresponding to the smaller openings; and the hinge-shaped stoppers are obtained by extending band-shaped elastic members in the direction along which the lancet-integrated sensor is impacted into the holder body, and bending the elastic members outward by 180°.

Accordingly, the holder body is attached to the measuring device with stability, by an extending force due to the elasticity of the stopper.

Further, according to a forty-third aspect of the present invention, in the measuring device for a lancet-integrated sensor which is defined in accordance with the forty-second aspect, each of the hinge-shaped stoppers has a clip member at a front end of the band-shaped elastic member, which clip member is thicker than the elastic member, and performs positioning when the holder body is latched in the opening.

Accordingly, a front end of each stopper is engaged with an inside of the smaller opening of the measuring device so as to prevent disconnection of the stopper from the smaller opening, whereby the holder body is attached to the measuring device with stability.

Further, according to a forty-fourth aspect of the present invention, there is provided a biosensor cartridge for housing plural biosensors, each having a reagent layer for detecting a specific component in bodily fluid of a subject, and an electrode for removing an electric signal indicating that the reagent layer detects the specific component, wherein a cartridge body has, at an end of its upper surface, a hinge for rotatably fixing a lid that covers the cartridge. The cartridge body has plural slits for perpendicularly supporting respective biosensor, and the plural slits are formed in parallel with each other, from an upper surface toward a lower surface of the cartridge body, at regular intervals which allow an insertion slot of a measuring device for performing measurement using a target biosensor to be inserted without touching biosensors adjacent the target biosensor.

Accordingly, a user can attach a sensor to the measuring device by only opening the lid and pressing the sensor insertion slot of the measuring device onto the sensor. Therefore, troublesome preparation for measurement, i.e., holding the sensor with hands to insert it into the measuring device for every measurement, is saved, resulting in improved usability.

Further, according to a forty-fifth aspect of the present invention, in the biosensor cartridge defined in accordance with the forty-fourth aspect, the cartridge body to which the lid is attached is a rectangular parallelepiped in shape.

Accordingly, the user can attach the sensor to the measuring device by only opening the lid and pressing the sensor insertion slot of the measuring device onto any of the sensors which are supported at regular intervals by the rectangular parallelepiped cartridge body. Therefore, troublesome preparation for measurement, i.e., holding the sensor with hands to insert it into the measuring device for every measurement, is saved, resulting in improved usability.

Further, according to a forty-sixth aspect of the present invention, in the biosensor cartridge defined in accordance with the forty-fifth aspect, the lid is a hollow rectangular parallelepiped in shape, and has an opening at a portion opposed to an upper surface of the cartridge body.

Accordingly, the user can attach the sensor to the measuring device by only opening the hollow and rectangular parallelepiped lid, and pressing the sensor insertion slot of the measuring device onto any of the sensors which are supported at regular intervals by the rectangular parallelepiped cartridge body. Therefore, troublesome preparation for measurement, i.e., holding the sensor with hands to insert it into the measuring device for every measurement, is saved, resulting in improved usability.

Further, according to a forty-seventh aspect of the present invention, in the biosensor cartridge defined in accordance with the forty-fourth aspect, a bottom of each slit has a shape that conforms to a shape of a front end of the biosensor.

Accordingly, the bottom of each slit of the cartridge body conforms to the shape of the front end of the biosensor so that no stress is applied to a specific portion of the front end of the biosensor, whereby the biosensor can be supported with reliability.

Further, according to a forty-eighth aspect of the present invention, in the biosensor cartridge defined in accordance with the forty-seventh aspect, the front end of the biosensor is semi-circular in shape.

Accordingly, the bottom of each slit of the cartridge body conforms to the semi-circular shape of the front end of the biosensor so that no stress is applied to a specific portion of the front end of the biosensor, whereby the biosensor can be supported with reliability.

Further, according to a forty-ninth aspect of the present invention, in the biosensor cartridge defined in accordance with the forty-fourth aspect: the hinge is constituted by a pair of bearings each having a side-to-side long bearing hole that projects outward along a longitudinal direction of the cartridge body from an end of the upper surface of the cartridge body, and a pair of axial projections which are provided at an end of the lid, and serve as fulcra when being smooth-movably engaged with the bearings to rotate the lid; a peripheral edge part is formed at a periphery of the upper surface of the cartridge body, which part extends in a direction perpendicular to side walls of the cartridge body, and has plural notches; reverse-L-shaped projections are formed on the same plane as the side walls of the lid, in positions corresponding to the notches of the peripheral edge part, at a periphery of the opening of the lid; and a sealing member having elasticity is formed on an upper surface of the peripheral edge part.

Accordingly, after the lid is closed, the lid is slid in the horizontal direction so that the reverse-L-shaped projections on the lid are engaged with the notches of the peripheral edge part of the cartridge body, whereby the sealing member having elasticity adheres closely to the edge of the opening of the lid and to the peripheral edge part of the cartridge body, and hermeticity in the cartridge is increased, thereby preventing the sensor from being contaminated with moisture.

Further, according to a fiftieth aspect of the present invention, there is provided a biosensor cartridge for housing plural lancet-integrated biosensors, each being constituted by integrating a biosensor having a reagent layer for detecting a specific component in bodily fluid of a subject, and an electrode for removing an electric signal indicating that the reagent layer detects the specific component, with a lancet for collecting the bodily fluid of the subject, wherein: the cartridge body has, at an end of its upper surface, a hinge for rotatably fixing a lid that covers the cartridge body; the cartridge body has plural grooves for perpendicularly supporting the lancet-integrated biosensors; and the plural grooves are formed in parallel with each other, from an upper surface toward a lower surface of the cartridge body, at regular intervals which allow an insertion slot of a measuring device for performing measurement using a target biosensor to be inserted without touching biosensors adjacent the target biosensor.

Accordingly, a user can attach the lancet-integrated sensor to the measuring device by only opening the lid and pressing the sensor insertion slot of the measuring device onto the sensor. Therefore, troublesome preparation for measurement, i.e., holding the lancet-integrated sensor with hands to insert it into the measuring device for every measurement, is saved, resulting in improved usability.

Further, according to a fifty-first aspect of the present invention, in the biosensor cartridge defined in the fiftieth aspect, the lancet-integrated biosensor includes: an approximately-square-shaped and narrow protector for protecting the lancet that projects from the lancet-integrated biosensor in its unused state; a sensor body in which the lancet is smooth-movably housed, the sensor body being approximately rectangular in shape, has a front end being semi-circular in shape, and is a little wider than the protector; and a connector which is provided on the lancet, protrudes backward from the sensor body, and has a width approximately equal to a width of the sensor body. Each of the plural grooves comprises a narrow first groove which is provided at a lowest surface side of the cartridge body, and conforms to the shape of the protector; a second groove which is wider than the first groove, is provided above the first groove, and conforms to the shape of a portion of the sensor body; and a third groove which is wider than the second groove, is provided above the second groove, and conforms to the shape of the insertion slot part of the measuring device into which the sensor body is inserted.

Accordingly, the lancet-integrated sensors each having a complicated shape can be supported at regular intervals, and a user can attach the lancet-integrated sensor to the measuring device by only pressing the sensor insertion slot of the measuring device onto the sensor. Therefore, troublesome preparation for measurement, i.e., holding the sensor with hands to insert it into the measuring device for every measurement, is saved, resulting in improved usability.

Further, according to a fifty-second aspect of the present invention, in the biosensor cartridge defined in accordance with the fifty-first aspect: the insertion slot stores the sensor body into a cavity which penetrates a pillar-shaped projection that projects from a side surface of the measuring device; and the connector is stored in the cavity that extends into the measuring device.

Accordingly, the user can attach the lancet-integrated sensor having a complicated rear-end shape to the measuring device by only pressing the sensor insertion slot of the measuring device onto the sensor. Therefore, troublesome preparation for measurement, i.e., holding the sensor with hands to insert it into the measuring device for every measurement, is saved, resulting in improved usability.

Further, according to a fifty-third aspect of the present invention, there is provided a measuring device for performing measurement using a lancet-integrated sensor that is attached thereto, with the lancet-integrated sensor being constituted by integrating a lancet for lancing skin to collect bodily fluid, and a sensor for analyzing extracted bodily fluid. The measuring device includes a drive device for driving the lancet in a direction in which the lancet lances the skin, along a longitudinal direction of the sensor, from a standby position of the lancet. After the drive device has driven the lancet in the direction in which the lancet lances the skin, the drive device can drive the lancet back to the standby position while maintaining a state where the lancet-integrated sensor is attached to the measuring device.

Accordingly, even when the lancet fails to lance the skin during a process of collecting bodily fluid, or measurement cannot be performed due to some problem, re-preparation for measurement can be easily performed, whereby usability of the measuring device for the lancet-integrated sensor is further improved.

Further, according to a fifty-fourth aspect of the present invention, in the measuring device for a lancet-integrated sensor which is defined in accordance with the fifty-third aspect, the drive device has a shaft to which a connector receiver is fixed at an end on a side where the lancet lances the skin, which connector receiver receives an end of the lancet on the side opposite to the side where the lancet lances the skin. A pull stick for driving the lancet back in a direction opposite to the direction in which the lancet lances the skin is disposed on an end of the shaft on the side opposite to the side where the lancet lances the skin, and the connector receiver is provided with a claw portion which is unlocked by pressing an operation button to start operation of the drive device, and stops motion of the connector receiver against a force applied by a spring that is provided on the shaft to move the connector receiver in the direction in which the lancet lances the skin.

Accordingly, even when the lancet fails to lance the skin during a process of collecting bodily fluid, or measurement cannot be performed due to some problem, re-preparation for measurement can be easily performed by operating the pull stick, whereby usability of the measuring device for the lancet-integrated sensor is further improved.

Further, according to a fifty-fifth aspect of the present invention, in the measuring device for a lancet-integrated sensor which is defined in accordance with the fifty-fourth aspect: the measuring device has, in its internal cavity, a support member for slidably supporting the shaft in the vicinity of its center; and the spring is a coil spring which is placed between the support member of the shaft and the connector receiver.

Accordingly, the shaft is supported in the measuring device, and the coil spring which is placed between the support member and the connector receiver supplies a force for driving the lancet.

Further, according to a fifty-sixth aspect of the present invention, in the measuring device for a lancet-integrated sensor which is defined in accordance with the fifty-fourth aspect: the pull stick has an opening which is formed at an end of the side where the lancet lances the skin; an end of the shaft on the side opposite to the side where the lancet lances the skin is slidably housed in the pull stick through the opening; and the end of the shaft on the side opposite to the side where the lancet lances the skin has a slip-out prevention member for preventing the end of the shaft from slipping out of the pull stick toward the side where the lancet lances the skin.

Accordingly, the shaft can be drawn out in the lancet projecting direction and in the opposite direction by pulling the pull stick.

Further, according to a fifty-seventh aspect of the present invention, in the measuring device for a lancet-integrated sensor which is defined in accordance with the fifty-fourth aspect, the driving device is provided with a lancet projection amount adjuster for adjusting an amount of projection of the needle of the lancet that lances the skin, which driving device is placed between the measuring device and the pull stick.

Accordingly, the amount of projection of the needle tip of the lancet is adjustable, whereby an amount of bodily fluid oozing out of the skin of the subject can be adjusted, or pain by being lanced with the lancet can be reduced.

Further, according to a fifty-eighth aspect of the present invention, in the measuring device for a lancet-integrated sensor which is defined in accordance with the fifty-seventh aspect: the pull stick is approximately cylindrical in shape, and an end of the pull stick on a side opposite to the side where the lancet lances the skin has a handle part having a portion of a diameter larger than a diameter of the cylindrical part; the lancet projection amount adjuster is approximately cylindrical in shape, and an end of the adjuster on the side opposite to the side where the lancet lances the skin has an opening having a diameter equal to the diameter of the cylindrical part of the pull stick; and the cylindrical part is slidably housed through the opening, and the cylindrical part is screwed into a screw hole that is formed on a side surface of the measuring device on the side opposite to the side where the lancet lances the skin, toward an inside of the measuring device, whereby the cylindrical part rotates in a screwing direction or in an opposite direction to adjust the amount of projection of the lancet.

Accordingly, the amount of projection of the needle tip of the lancet is adjustable, whereby an amount of the bodily fluid oozing out of the skin of the subject can be adjusted, or pain by being lanced with the lancet can be reduced.

BRIEF DESCRIPTION OF THE DRAWINGS

FIGS. 1(a) and 1(b) are diagrams illustrating a lancet-integrated sensor according to a first embodiment of the present invention, wherein FIG. 1(a) is a perspective view of the lancet-integrated sensor in its entirety, and FIG. 1(b) is an exploded perspective view thereof.

FIGS. 2(a)-2(d) are plan views for explaining operation of the lancet-integrated sensor, wherein FIG. 2(a) shows a state where a needle tip, which is covered with a protection cover, protrudes from the sensor, FIG. 2(b) shows a state where the needle tip, which is covered with the protection cover, is housed in the sensor, FIG. 2(c) shows a state where the needle tip, from which the protection cover is removed, protrudes from the sensor, and FIG. 2(d) shows a state where the needle tip, from which the protection cover is removed, is housed in the sensor.

FIGS. 3(a) and 3(b) are perspective views of a measuring device to be combined with the lancet-integrated sensor according to the first embodiment of the invention, wherein FIG. 3(a) shows an upper surface of the measuring device, and FIG. 3(b) shows a lower surface thereof.

FIGS. 4(a) and 4(b) are diagrams for explaining an internal structure of the measuring device, wherein FIG. 4(a) is an exploded perspective view of a lower half side of the measuring device, and FIG. 4(b) is a cross-sectional view of a side surface thereof.

FIGS. 5(a)-5(c) are diagrams for explaining an operation for attaching the lancet-integrated sensor to the measuring device, wherein FIG. 5(a) is a sectional side elevation view at a starting of attachment, FIG. 5(b) is a sectional side elevational view at completion of the attachment, and FIG. 5(c) is a sectional view in the vicinity an operation button.

FIGS. 6(a) and 6(b) are diagrams illustrating a protection cover of the lancet-integrated sensor according to the first embodiment of the invention, wherein FIG. 6(a) shows a state where the protection cover is fitted when the needle tip protrudes, and FIG. 6(b) shows a state where the protection cover is fitted to a front end of the sensor when the needle tip is housed.

FIGS. 8(a) and 8(b) are diagrams illustrating a lancet-integrated sensor according to a second embodiment of the invention, wherein FIG. 8(a) shows a perspective view of the lancet-integrated sensor in its entirety, and FIG. 8(b) is an exploded perspective view thereof.

FIGS. 9(a) and 9(b) are diagrams illustrating the lancet-integrated sensor according to the second embodiment of the invention and a measuring device for the lancet-integrated sensor, wherein FIG. 9(a) is a perspective view of the measuring device in a state where the sensor is attached thereto, and FIG. 9(b) is a cross-sectional view of the measuring device in a state where the sensor is attached thereto.

FIGS. 11(a) and 11(b) are diagrams illustrating an appearance of a measuring device for a lancet-integrated sensor according to a third embodiment of the invention, wherein FIG. 11(a) shows a state where a holder is attached, and FIG. 11(b) shows a state where the holder is removed.

FIGS. 12(a)-12(c) are diagrams illustrating an appearance of the holder of the measuring device for a lancet-integrated sensor according to a third embodiment of the invention, wherein FIG. 12(a) is an elevational view in a state where the holder is attached to the measuring device, FIG. 12(b) is a cross-sectional view when the holder attached to the measuring device is viewed from above, and FIG. 12(c) is a cross-sectional view when the holder to be removed from the measuring device is viewed from above.

FIGS. 13(a) and 13(b) are diagrams illustrating an internal structure of a measuring device which uses a lancet-integrated sensor according to the third embodiment of the invention, and another construction of a lancet-integrated sensor, wherein FIG. 13(a) is a cross-sectional view of the measuring device in a state where the holder is attached, and FIG. 13(b) is a partially cutaway cross-sectional view of the measuring device in a state where the holder is attached.

FIGS. 17(a) and 17(b) are diagrams illustrating a state where a sensor stored in the biosensor cartridge according to the fifth embodiment of the invention is inserted into a measuring device, wherein FIG. 17(a) shows a state where the sensor is inserted, and FIG. 17(b) shows a state before the sensor is inserted.

FIGS. 18(a)-18(c) are diagrams illustrating a biosensor cartridge according to a first modification of the fifth embodiment of the invention, wherein FIG. 18(a) is a perspective view illustrating a state where a lid is opened, FIG. 18(b) is a side view illustrating a state where the lid is closed, and FIG. 18(c) is a cross-sectional view illustrating a state where the lid is closed.

FIGS. 20(a) and 20(b) are diagrams for explaining attachment of a lancet-integrated sensor to a measuring device in the biosensor cartridge according to the second modification of the fifth embodiment of the invention, wherein FIG. 20(a) is a diagram illustrating a state where the sensor is attached, and FIG. 20(b) is a diagram illustrating a state before the sensor is attached.

FIGS. 22(a) and 22(b) are diagrams illustrating a conventional lancet device, wherein FIG. 22(a) is a perspective view thereof, and FIG. 22(b) is a perspective view thereof in a state where a part of the lancet device is seen through.

FIGS. 23(a) and 23(b) are diagrams illustrating a conventional manner of housing biosensors, wherein FIG. 23(a) shows a state where a biosensor is wrapped with a wrapper, and FIG. 23(b) shows a state where plural biosensors are stored in a plastic container.

FIG. 24 is a diagram illustrating a state where a biosensor is inserted into a measuring device.

DETAILED DESCRIPTION OF THE PREFERRED EMBODIMENTS

Embodiment 1

Figure 1:
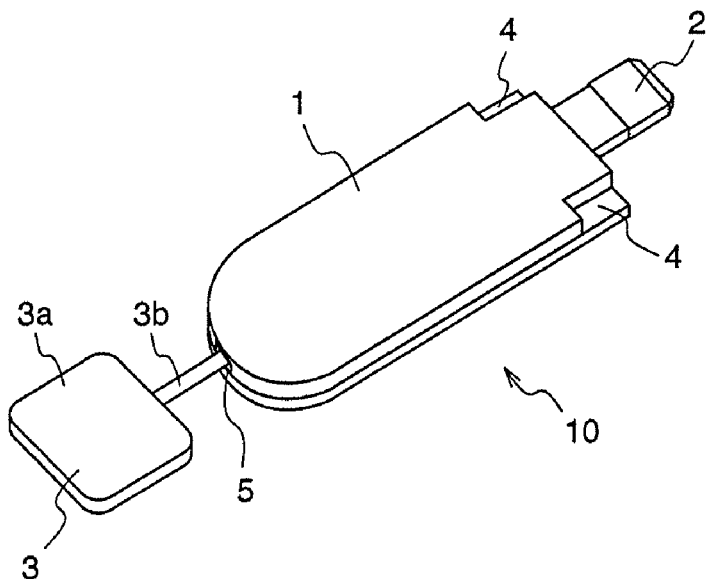
Figure 1:
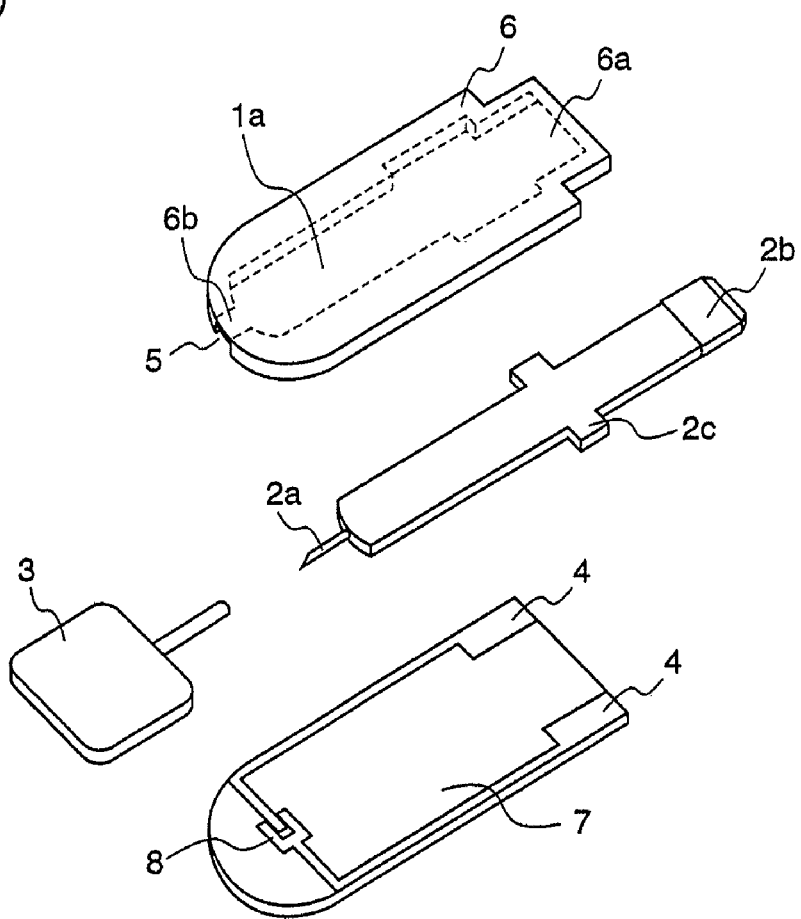

Hereinafter, a first embodiment of the present invention will be specifically described taking, as an example, a blood sugar sensor for electrochemically measuring blood sugar, with reference to the drawings.

The first embodiment relates to a lancet-integrated sensor in which a lancet and a sensor are integrated to facilitate management and carrying, and a measuring device for driving the lancet-integrated sensor, and performing measurement using the sensor.

That is, in the lancet-integrated sensor according to the first embodiment, a long and narrow strip-shaped sensor and a lancet are integrated with each other and, more specifically, the lancet is horizontally movable along a longitudinal direction of the sensor.

The measuring device, to which the lancet-integrated sensor is fitted, is provided with a lancet driving function of a conventional lancet device. That is, the measuring device is provided with a driving member for driving the lancet of the lancet-integrated sensor that is fitted thereto.

In this construction, a patient sets a new lancet-integrated sensor onto the measuring device every time he/she performs measurement. Then, the patient grips the measuring device, and turns on the lancet driving member to lance his/her fingertip with the lancet. Subsequently, the patient drops blood onto the sensor to measure blood sugar or the like.

Hereinafter, the lancet-integrated sensor and the measuring device will be described more specifically.

FIGS. 1(a) and 1(b) are a perspective view and an exploded perspective view of a lancet-integrated sensor according to the first embodiment of the invention, respectively. With reference to FIG. 1(a), numeral 10 denotes a lancet-integrated sensor, wherein numeral 1 denotes a long and narrow strip-shaped sensor, and numeral 2 denotes a lancet, a greater part of which is housed in a hollow (space) 1a in the sensor 1, and the lancet 2 is supported by the sensor (sensor body) 1 so as to be slidable in a longitudinal direction of the sensor 1.

Reference numeral 3 denotes a protection cover into which a needle tip of the lancet 2 is pressed, thereby protecting the needle tip. This cover 3 is removed during measurement. Reference numeral 4 denotes electrode terminals for making electrical connection with a measuring device which is later described. Reference numeral 5 denotes a cavity provided at a semi-circular front end of the sensor 1.

As shown in FIG. 1(b), construction of the sensor 1 is obtained by bonding a cover (plate) 6 to a substrate (plate) 7, which are made of a resin such as polyethylene terephthalate. Further, the lancet 2 comprises a metal needle 2a, and a connector (end portion) 2b which has the needle 2a at its front end, and holds the needle 2a. A rear end portion of the strip-shaped connector 2b projects from a rear end of the sensor 1 to be engaged with the driving member of the measuring device which is described later.

At a lower surface of the cover 6, concave portions which conform to a shape of the lancet 2 are provided. More specifically, there are provided a groove (concave portion) 6a which conforms to an outline of the connector 2b so that the connector 2b is slidably housed therein along its longitudinal direction, and a long and narrow groove (concave portion) 6b in which the needle 2a is housed. The groove 6b in which the needle 2a is housed is extended to the front end of the sensor 1. Further, a pair of electrodes 8 leading to the electrode terminals 4 are formed on a surface of the substrate 7, and a reagent layer (not shown) is formed on a surface of the electrodes 8.

In this way, the lancet-integrated sensor is obtained by bonding the cover 6 and the substrate 7 together, with the lancet 2 being placed therebetween. Accordingly, the cavity 5 also serves as the long and narrow groove 6b into which the needle 2a is housed. Further, portions of the electrodes 8 and the reagent layer are exposed in the cavity 5.

As described above, the lancet 2 is movable along the longitudinal direction of the sensor 1, and its motion will be described hereinafter with reference to a plan view shown in FIGS. 2(a)-2(d).

Figure 2:
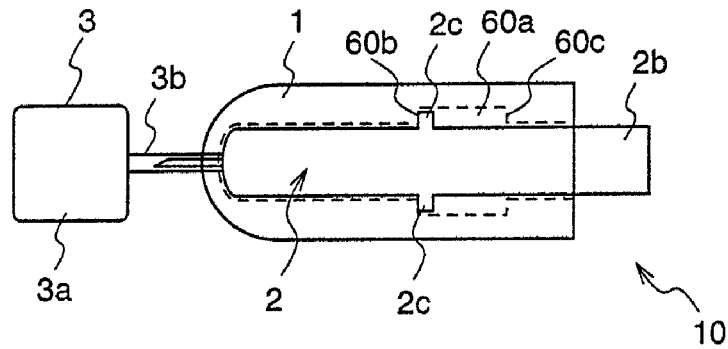
Figure 2:
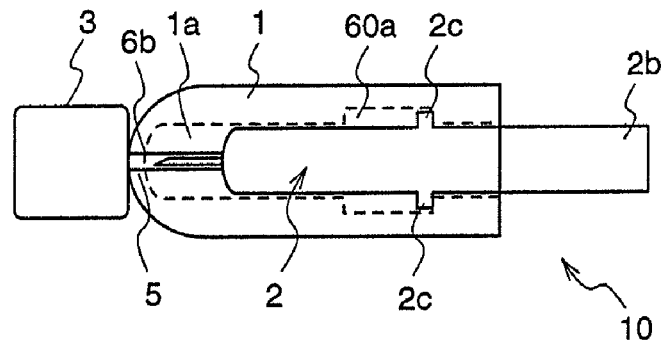
Figure 2:
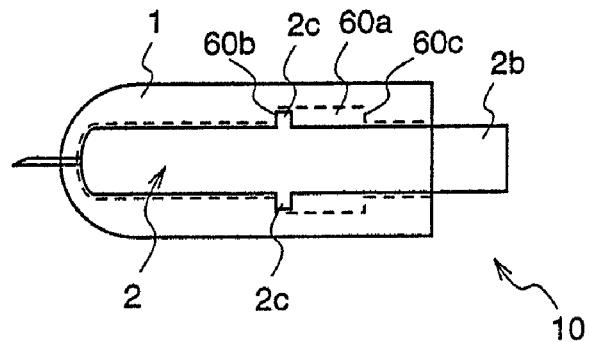
Figure 2:
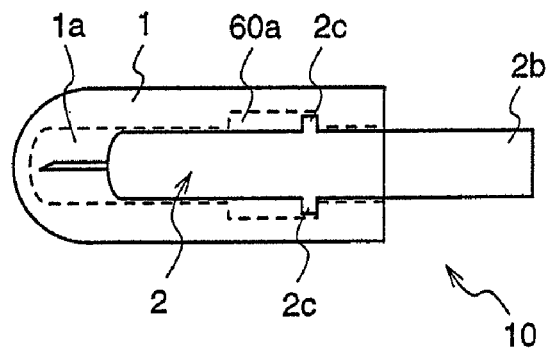

FIG. 2(a) shows a state where a position of the lancet 2 is closest to the front end of the sensor 1. That is, each of fine projections 2c, which are formed so as to project from the connector 2b in a direction perpendicular to a longer side of the connector 2b within the same plane as a main surface of the connector 2b, abuts a side wall 60b at an end of a wide concave groove (concave portion) 60a on a topmost side of the sensor 1, which groove 60a is formed in the cover 6. In this state, a longest portion of the needle 2a of the lancet 2 projects from the front end of the sensor 1. FIG. 2(b) shows a state where each of the fine projections 2c of the connector 2b abuts a side wall 60c at an end of the concave groove 60a on a rearmost side of the sensor 1. In this state, the needle of the lancet 2 is completely housed in the sensor 1.

As shown in FIGS. 2(a) and 2(b), a shape of the groove 60a is curved such that, at an end where the fine projection 2c is positioned, a width of the groove 60a is a little narrower than a width of the connector 2b including the fine projection 2c. Accordingly, at the end of the concave groove 60a, the connector 2b is latched by the sensor 1 due to mutual pressing or friction.

The construction of the lancet-integrated sensor is as described above, and the protection cover 3 is removed for measurement, and a fingertip or the like is lanced with the tip of the needle 2a of the lancet 2 which projects from an opening of the cavity 5, as shown in FIG. 2(c). When blood is dropped onto the sensor 1 and sucked into the cavity 5 to measure blood sugar as shown in FIG. 2(d), the needle tip of the lancet 2 is positioned in the groove 6a which is apart from the cavity 5 so that the needle does not contact the blood sucked into the cavity 5.

Measuring Device

Next, an example of a measuring device to be connected with the above-described lancet-integrated sensor will be described with reference to the drawings.

Figure 3:
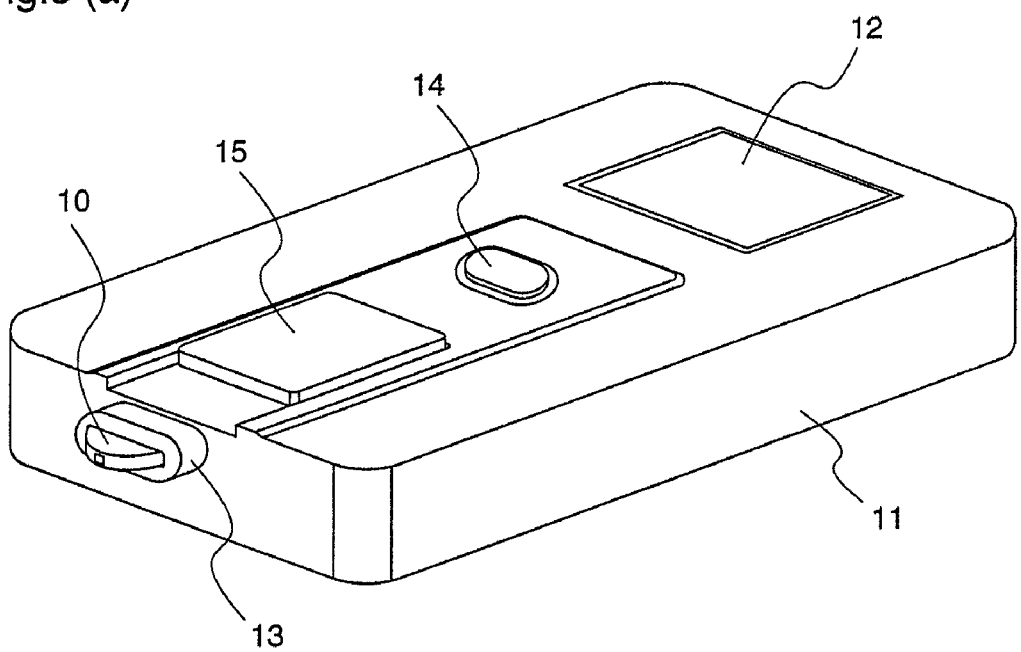
Figure 3:
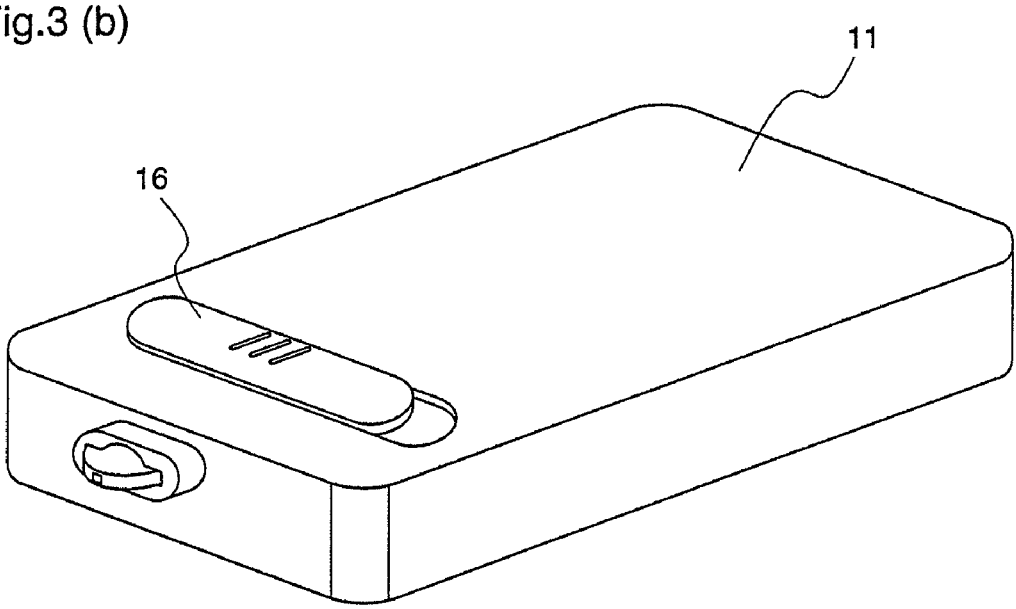

FIGS. 3(a) and 3(b) are perspective views of a measuring device 11 to which a lancet-integrated sensor is fitted, and FIG. 3(a) mainly shows its upper surface while FIG. 3(b) mainly shows its lower surface. Reference numeral 12 denotes a display (display device) for displaying a result of measurement and the like, and numeral 13 denotes a slot into which the lancet-integrated sensor is inserted. Reference numeral 14 denotes a push button (unlocking member) for driving the lancet that is fitted to the measuring device 11 such that the lancet forcibly projects to lance a fingertip or the like. Further, reference numeral 15 denotes a slide button (ejection member, operation button) for ejecting a used lancet-integrated sensor from the measuring device 11. Further, reference numeral 16 denotes an adjustment button (lancet projection amount adjuster) for adjusting an amount of projection of the needle tip of the lancet.

Figure 4:
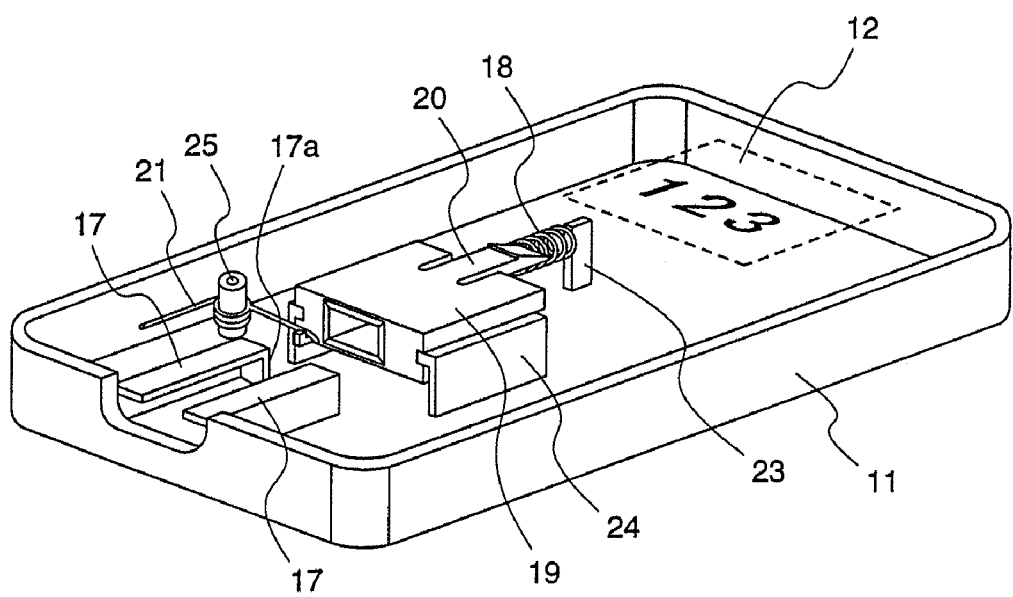
Figure 4:
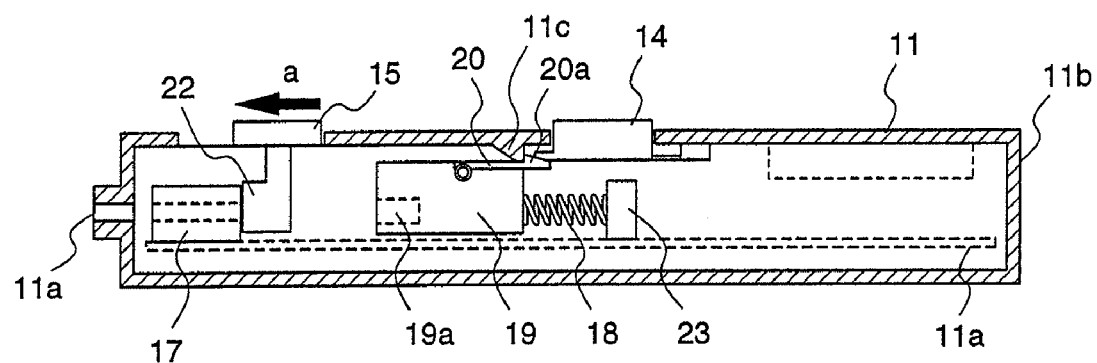

FIG. 4(a) is a perspective view of the measuring device 11 in a state where an upper portion of a package case is removed to show an internal structure of the measuring device 11, and FIG. 4(a) specifically shows a connection terminal to be electrically connected with the sensor, and the driving member to be engaged with the connector of the lancet. Further, FIG. 4(b) is a side view of the measuring device.

Reference numeral 17 denotes a pair of guides having connection terminals to be electrically connected with the electrode terminals of the sensor. The guides 17 are planted on substrate 11a at a bottom of the package case by resin molding so as to have approximately-L-shaped cross sections, and connection terminals are formed on ceilings of the guides 17. Further, at an end of each guide 17, which is opposite to a connector receiver 19, a termination member 17a is planted to make a dead-end, excluding a space between the guides 17. When fitting the lancet-integrated sensor to the measuring device, the sensor 10 is guided by the guides 17 to be set.

Reference numeral 18 denotes a coil spring (lancet pushing member) for driving the lancet 2, and numeral 19 denotes the connect receiver (lancet pushing member) which is engaged with the connector 2b of the lancet 2. The connector receiver 19 is slidably supported by a pair of approximately-inverse-L-shaped supporting members 24 which are planted on the substrate 11a, and an end of the coil spring 18 is fixed onto a side of the connector receiver 19, which is opposite to a side that is engaged with the sensor 10. Another end of the coil spring 18 is supported by a spring stopper (lancet pushing member) 23. When the lancet 2 is engaged with the connector receiver 19 and the lancet 2 is pushed into the measuring device 11, the coil spring 18 is compressed, whereby a force for driving the lancet 2 is applied to the coil spring 18.

Reference numeral 20 denotes a driving lever having a tapered projection 20a which is engaged with a tapered projection 11c that is positioned in front of the push button 14. When the lancet 2 is set up to a predetermined position, the driving lever 20 latches the connector receiver 19 to hold a driving force. This latching is canceled by pushing the push button 14, and the lancet 2 is driven by a pressing force from the spring 18.

Reference numeral 21 denotes a torsion spring for restricting a position of the connector receiver 19, and the torsion spring 21 is fixed by a shaft member 25 that is planted in the vicinity of a side surface parallel with an insertion path of the sensor 10. The torsion spring 21 pushes the connector receiver 19 that is not latched by the driving lever 20, in a direction against elasticity of the coil spring 18. The torsion spring 21 restricts a position of the connector receiver 19, in balance with the elasticity of the coil spring 18, so that the needle tip of the lancet 2 is positioned apart from the cavity 5 to prevent the needle tip from contacting blood drawn into the cavity 5.

Reference numeral 22 denotes an ejection lever which is united with the slide button 15, and the ejection lever 22 pushes a rear end of the sensor 1 to eject the sensor 1 from the measuring device when the slide button 15 is operated in a direction indicated by arrow a.

Measuring Operation

Hereinafter, a description will be given of a series of measuring operations, with respect to the lancet-integrated sensor and the measuring device, which are constructed as described above.

Initially, an operation for fitting the lancet-integrated sensor to the measuring device will be described. The lancet-integrated sensor is in a state shown in FIG. 2(a) when it is not used. That is, the needle tip of the lancet 2 projects from the sensor 1, and is covered with the protection cover 3. A patient grips a wide grip part 3a of the protection cover 3, and inserts the lancet 2, from a connector 2b side, into the insertion slot 13 of the measuring device 11.

Figure 5:
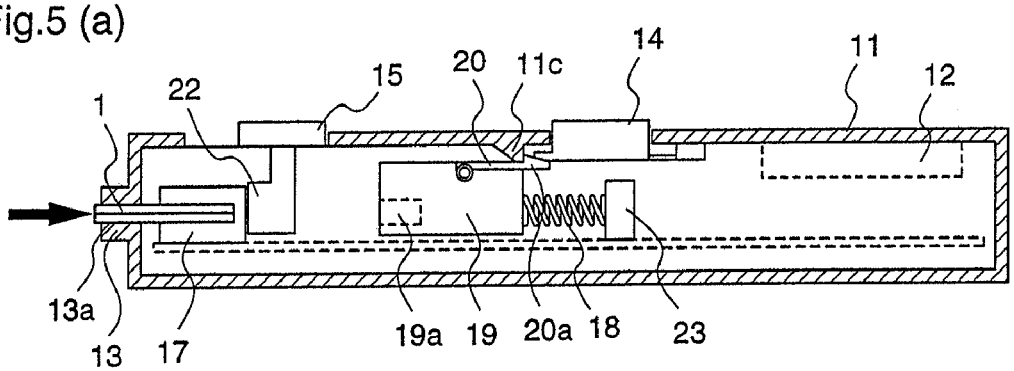
Figure 5:
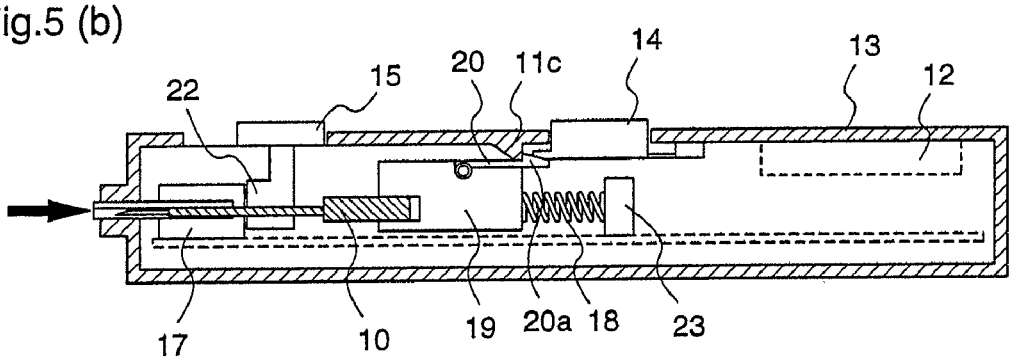
Figure 5:
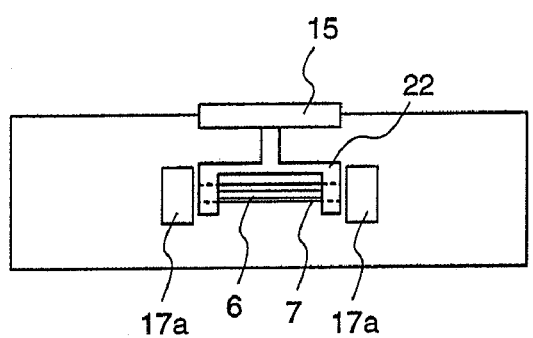

The patient further pushes the grip part 3a of the protection cover 3 to insert the sensor 1 and the lancet 2 deeper into the measuring device 11. Thereby, as shown in FIG. 5(a), the sensor 1 is guided by the guide 17 to advance into a case 11b. As the sensor 1 continues to advance into the case, a shorter side of the sensor 1, which is opposite to the semi-circular side thereof, touches the termination member 17a of the guide 17 to be set at a fixed position where advance of the sensor 1 into the case 11b is restricted, whereby the electrode terminals 4 of the sensor 1 are connected to the connection terminals (not shown) of the measuring device 11. In order to make FIG. 5(a) easy to see, only the sensor 1 of the lancet-integrated sensor is shown, and a part corresponding to the lancet 2 is omitted.

Although advance of the sensor 1 is stopped at this point of time, since motion of the lancet 2 is not restricted by the termination members 17a of the guides 17 as shown in FIG. 5(c), the lancet 2 can be inserted deeper into the case 11b. That is, by a pressing force of the protection cover 3, the engagement of the fine projections 2c with the concave groove 60a is released at the position shown in FIG. 2(a). Then, as shown in FIG. 2(b), the tube 3b of the protection cover 3, which protects the needle 2a, is pushed into the sensor 1, and a side of the grip part 3a of the protection cover 3 touches the front end of the sensor 1.

When the patient pushes the protection cover 3 deeper than the state shown in FIG. 5(a), the connector 2b of the lancet 2 is engaged with concave portion 19a of the connector receiver 19 and, as shown in FIG. 5(b), the coil spring 18 is compressed, whereby tapered projection 20a of the driving lever 20 of the connector receiver 19 is latched by tapered projection 11c in front of the push button 14 to complete fitting of the sensor 10.

Next, a blood collecting operation and a blood dropping operation will be described. FIG. 3(a) shows a state where fitting of the lancet-integrated sensor to the measuring device is completed. The patient holds the measuring device 11, and lightly pushes the front end of the sensor 10 against a portion of his/her body from which blood is to be extracted, such as a fingertip.

When the patient pushes the push button 14, the lancet 2 is driven, and the needle tip forcibly projects from the front end of the sensor 10 to lance skin of the patient. At this time, an amount of projection of the needle tip from the sensor is variable by sliding the adjustment button 16 in a horizontal direction. To be specific, the torsion spring 21 is moved in the horizontal direction in the measuring device 11 by sliding the adjustment button 16 in the horizontal direction, thereby to adjust a spring force. Alternatively, a distance between the connector receiver 19 that is engaged with the push button 14, and the spring stopper 23 is increased or reduced by driving a mechanism (not shown) for converting motion of the adjustment button 16 in the horizontal direction into a to-and-fro motion of the spring stopper 23 along a driving direction of the lancet 2. The amount of projection can be displayed on the display unit 12 by converting an amount of sliding of the adjustment button 16 to an amount of projection using a CPU or the like of the measuring device.

The patient drops a small amount of blood that is oozing from a lanced fingertip, for example, onto the front end of the sensor 10, and this dropped blood is drawn into the cavity 5 by capillary phenomenon. The measuring device 11 measures blood sugar with an internal electronic circuit, and displays a result of this measurement on the display unit 12. When the result of measurement is displayed to end measurement, the patient slides the slide button 15 in a direction toward which the lancet 2 projects, whereby the lancet-integrated sensor is ejected from the measuring device 11, and this ejected lancet-integrated sensor is disposed of.

At this point of time, the connector 2b of the lancet 2 is engaged with the connector receiver 19 of the measuring device 11 although the ejection lever 22 pushes the rear end of the sensor 1. Since the sensor 1 is ejected first, a positional relationship between the sensor 1 and the lancet 2 goes into a state shown in FIG. 2(d). Then, the fine projections 2c of the lancet 2 are engaged with the concave groove 60a, and the lancet-integrated sensor is ejected from the measuring device 11 with the needle tip of the lancet 2 being completely housed in the sensor 1. Therefore, it is possible to prevent injury or infectious disease caused by the needle tip protruding from the sensor.

As described above, according to the first embodiment of the invention, since the sensor and the lancet are integrated with each other, management thereof is facilitated, and trouble of separately replacing the sensor and the lancet at every use is saved. Further, since the sensor and the lancet can be simultaneously set in the measuring device, setting is facilitated, and this unit in its entirety is reduced in size and is easy to carry.

Figure 6:
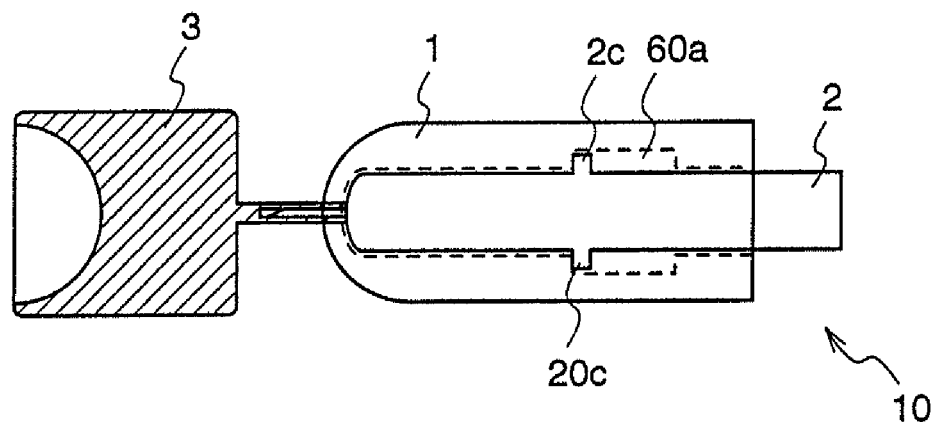
Figure 6:
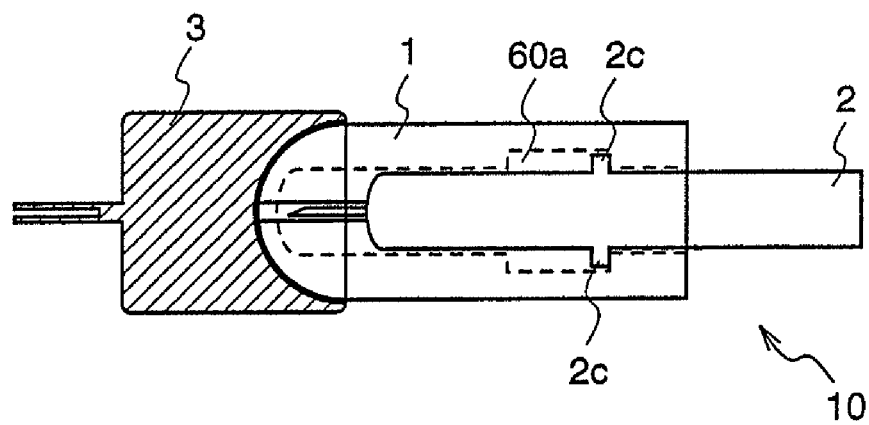

When the lancet-integrated sensor is ejected, in order to prevent injury and infectious disease more reliably, a semi-circular space that conforms to the shape of the front end of the sensor 1 is formed on a side of the grip part 3a of the protection cover 3 as shown in FIG. 6(a), and the lancet-integrated sensor may be ejected with the sensor 1 being covered with the protection cover 3 as shown in FIG. 6(b).

Further, while the lancet-integrated sensor according to the first embodiment is provided with the protection cover that covers the tip of the lancet, the lancet-integrated sensor may be provided with a holder which covers a periphery of the lancet-integrated sensor and the protection cover to hold these members. In this case, fitting of the lancet-integrated sensor to the measuring device and ejection of the sensor from the measuring device can be performed with the sensor being covered with the holder, and operation is eased for patients with manual impairments.

When the holder is formed of a transparent material to make it easy to see an internal lancet-integrated sensor, operability is further enhanced.

Furthermore, while in the first embodiment the lancet-integrated sensor uses space in which the needle tip of the lancet moves, also with regard to the cavity into which blood is drawn, the space and the cavity may be separated. Further, while in this first embodiment the sensor is a thin plate in shape, the shape of the sensor is not restricted thereto, and the sensor may be cylindrical in shape.

Figure 7:
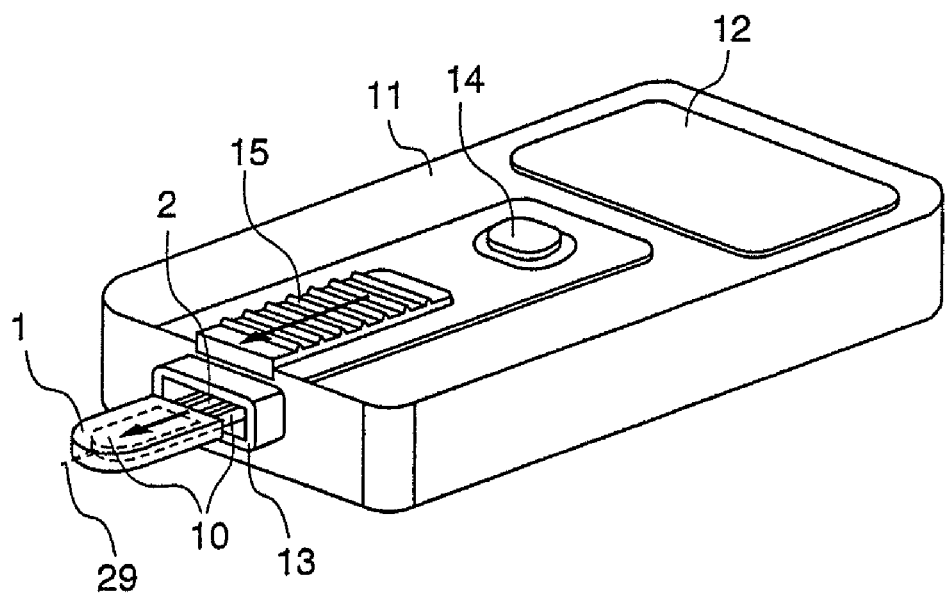
FIG. 7 is a perspective view of a measuring device to be combined with the lancet-integrated sensor according to the first embodiment of the invention.

Furthermore, as shown in FIG. 7, the slide button 15 of the measuring device 11 may have wave-shaped projections and depressions on its upper surface to prevent a finger from slipping, and a shape of the sensor insertion slot 13 may approach a rectangle.

Embodiment 2

According to a second embodiment of the invention, when the lancet-integrated sensor is disconnected from the measuring device, the tip of the needle 2a is reliably housed in the sensor to prevent the possibility that a finger of another person touches the needle 2a onto which a bodily fluid remains, or a person pricks his/her finger with the needle 2a by mistake, thereby avoiding infectious disease as well as problems in terms of safety.

Hereinafter, a description will be given of a lancet-integrated sensor, and a measuring device which performs a measurement using this lancet-integrated sensor.

Figure 8:
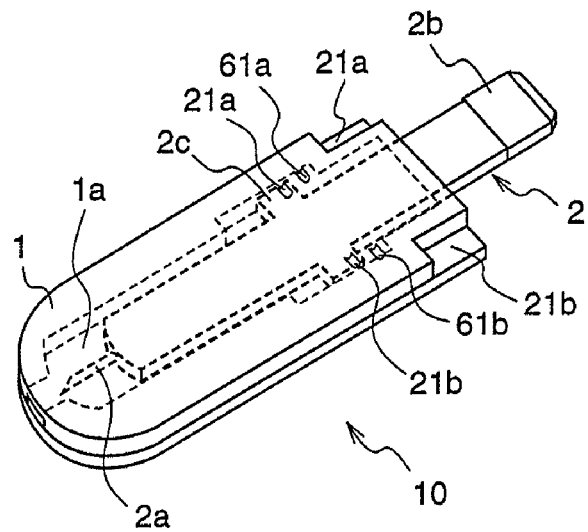
Figure 8:
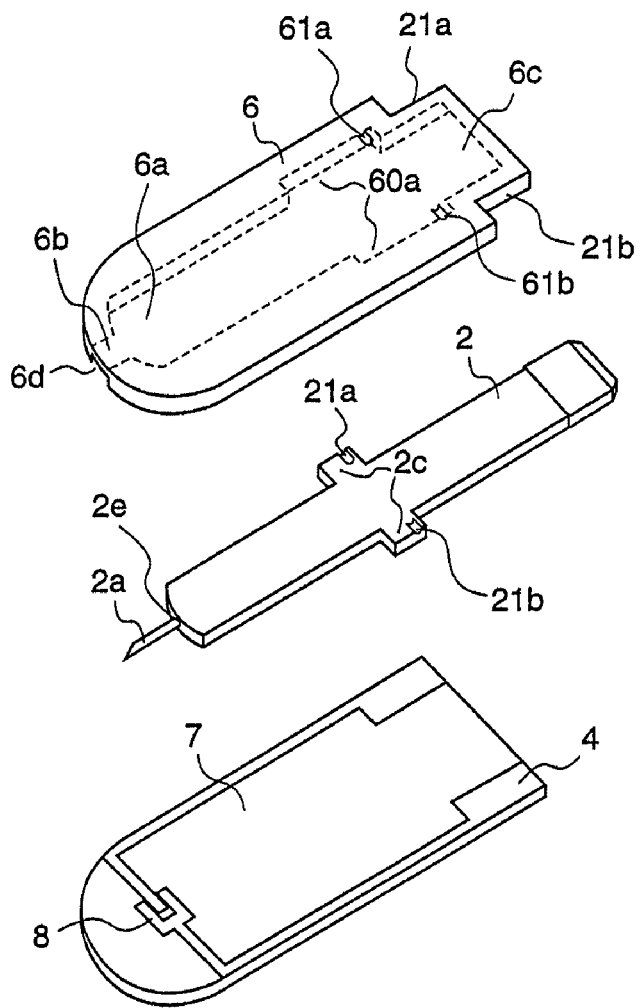
Figure 9:
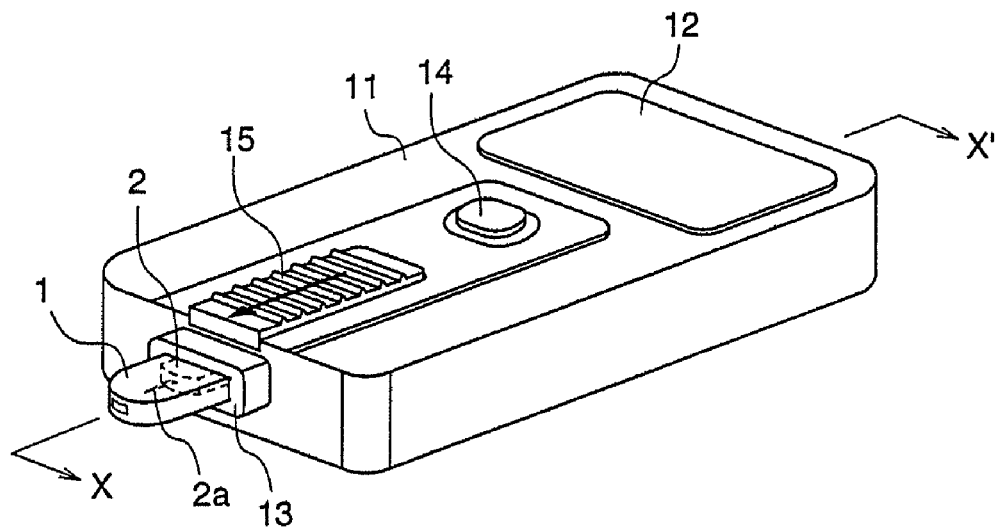
Figure 9:
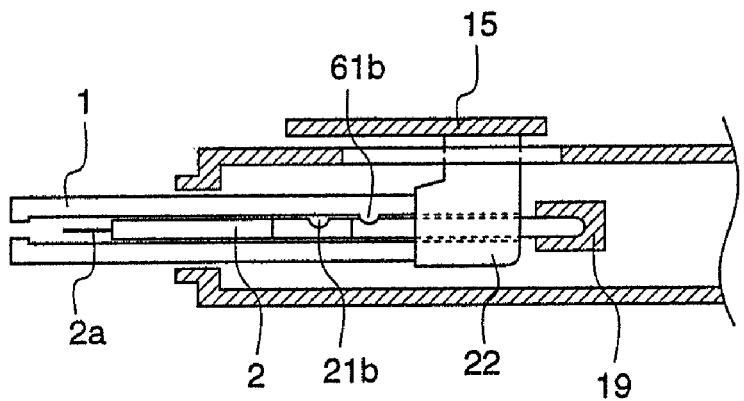

FIG. 8(a) is a perspective view illustrating an example of a lancet-integrated sensor according to the second embodiment of the invention.

With reference to FIG. 8(a), reference numeral 2 denotes a lancet for lancing skin of a man or an animal to extract bodily fluid. The lancet 2 is composed of a connector 2b which is made of an approximately rectangular-shaped plate member, and a needle 2a for lancing the skin, which is provided at a head of the connector 2b, i.e., in the vicinity of a center of a semi-circular-shaped shorter side of the connector 2b having two shorter sides. In the vicinity of a center of two longer sides of the connector 2b, small-sized fine projections 2c are formed at right angles from respective longer sides, and these fine projections 2c have, on their upper surfaces, fine concave portions 21a and 21b (concave portions for locking, locking members) which are somewhat long from side to side and have semi-cylindrical-shaped bottom surfaces. Reference numeral 1 denotes a sensor for analyzing extracted bodily fluid. The sensor 1 has an internal cavity 1a in which the lancet 2 is slidably housed. The sensor 1 has, at a ceiling of the cavity 1a, fine convex portions 61a and 61b (convex portions for locking, locking members) which are somewhat long from side to side and have semi-cylindrical-shaped surfaces, to be engaged with the fine concave portions 21a and 21b provided on the fine projections 2c of the lancet 2, respectively. Reference numeral 1a denotes a cavity formed in the sensor 1. The cavity 1a has a width a little larger than a width of the lancet 2, and has a pair of concave grooves 60a that project from two longer sides of the cavity 1a, in a width direction, correspondingly to the fine projections 2c of the lancet 2. Reference numeral 2a denotes a needle for lancing the skin, which is provided at a front end 2e of the lancet 2, i.e., in the vicinity of a center of a somewhat-rounded shorter side (head side) of two shorter sides of the lancet 2. Reference numeral 10 denotes a lancet-integrated sensor, in which the lancet 2 and the sensor 1 are integrated with each other.

FIG. 8(b) is an exploded perspective view illustrating an example of a lancet-integrated sensor according to the second embodiment of the invention.

As shown in FIG. 8(b), the lancet-integrated sensor 10 is constituted by placing the lancet 2 between a cover 6 and a substrate 7 which are components of the sensor 1, and bonding the cover 6 and the substrate 7 together.

The cover 6 has a groove 6a whose outline shape is a little larger than that of the lancet 2, and the groove 6a forms a cavity 1a in which the lancet 2 is to be housed slidably along its longitudinal direction. In the groove 6a, concave grooves 60a for restricting a region where the lancet 2 is slidable are formed on a rear portion of longer sides of the groove 6a so that a part with the concave grooves 60a becomes a little wider than another part of the groove 6a, and a length of each concave groove 60a in a transverse direction is set according to a length of the fine projections 2c of the lancet 2.

Further, as described above, the fine concave portions 21a and 21b of the lancet 2 are formed on the upper surfaces of the fine projections 2c which are formed in the vicinity of the center of the longer sides of the lancet 2, in positions most distant from the needle 2a, i.e., in the vicinity of edges of the projections 2c on an opposite side from the needle 2a. The fine convex portions 61a and 61b of the sensor 1 are formed in ceilings of the concave grooves (hollows) 60a of the cover 6, in positions most distant from the needle 2a when the lancet-integrated sensor is assembled, i.e., in the vicinity of edges of the concave grooves 60a on the opposite side from the needle 2a.

Although a positional relationship between the fine concave portions 21a and 21b and the fine convex portions 61a and 61b may be other than mentioned above, these portions must be arranged with a predetermined positional relationship such that the needle 2a of the lancet 2 is housed in the sensor 1 when the fine concave portions 21a and 21b of the lancet 1 are engaged with the fine convex portions 61a and 61b of the concave grooves 60a of the cover 6.

Further, a front end of the cover 6, i.e., a shorter side of the cover 6 facing the needle 2a of the lancet 2, is semi-circular in shape, and a groove 6b, an end of which is connected to the groove 6a, is formed at the front end of the cover 6 so that the needle 2a at front end 2e projects from the sensor 1, and another end of the connecting groove 6b is an opening 6d of the front end of the sensor 1. An opening 6c is also formed on a rear end of the cover 6, i.e., an end of the cover 6 on the side opposite to the needle 2a of the lancet 2, so that the connector 2b of the lancet 2 projects from the sensor 1, and notches 21a and 21b are formed at two corners of the rear end of the cover 6 so that electrode terminals 4 are exposed.

Although a front end of the substrate 7 is semi-circular in shape like the cover 6, the substrate 7 has no notches on a the rear end unlike the cover 6. On a surface of the substrate 7, the two electrode terminals 4 are formed at two corners of rear ends of the longer sides, and a pair of electrodes 8 connected to the electrode terminals 4 by wiring are formed in the vicinity of a center of the semi-circular part on the front end of the substrate 7. Further, a reagent layer (not shown) is formed on a surface of the electrodes 8. The lancet-integrated sensor 10 is completed by bonding the cover 6 to the substrate 7, with the lancet 2 being housed in the groove 6a of the cover 6 as described above.

A protection cover 3 is fitted to the lancet-integrated sensor according to the second embodiment of the invention as shown in FIGS. 2(a) and 2(b). Further, a measuring device for the lancet-integrated sensor according to the second embodiment of the invention has the same outward shape as that shown in FIGS. 3(a) and 3(b). An internal structure of the measuring device is the same as that shown in FIGS. 4(a) and 4(b) and FIGS. 5(a), 5(b), and 5(c).

Next, a series of measuring operations of the lancet-integrated sensor and the measuring device which are completed as described above, will be described.

Initially, an operation of attaching the lancet-integrated sensor to the measuring device will be described. In a state where the lancet-integrated sensor is not used, the lancet 2 is placed in such a position that the needle tip projects from the sensor 1, and the needle tip is covered with the protection cover 3, as shown in FIG. 2(a). The protection cover 3 is composed of a tube 3b as a needle housing part, and an approximately-square-shaped grip part 3a. A user holds this wide grip part 3a of the protection cover 3, and inserts a rear end of the connector 2b of the lancet 2 (an end of the lancet 2 opposite to the needle) from opening 13a of insertion slot 13 of the measuring device 11, as shown in FIG. 2(a).

At this time, as shown in FIG. 5(a), the rear end of the connector 2b of the lancet 2 is guided by guide (guide member) 17 in the measuring device 11, and goes toward concave portion 19a of a front end of connector receiver 19. The connector receiver (lancet pushing member) 19 is pressed in opposite directions by coil spring 18 and torsion spring 21, and stands still in a position where pressing forces are balanced.

As the user continues to insert the lancet-integrated sensor 10 with the lancet 2 being covered with the protection cover 3, initially the lancet 2 is gradually inserted together with the sensor 1 to reach a position where it contacts ejection lever 15 that is united with slide button 14. Thereafter, when the slide button 14 reaches an end of its movable range (display 13 side) that is restricted by the termination member 17a of the guide 17, the sensor 1 stops its backward movement. On the other hand, the lancet 2 moves back in the sensor 1 while the user pushes the protection cover 3.

When the lancet 2 reaches an end of its movable range in the sensor 1, the fine concave portions 21a and 21b of the lancet 2 are engaged with the fine convex portions 61a and 61b of the cover 6 of the sensor 1 as shown in FIG. 2(b), whereby the lancet 2 is locked with respect to the sensor 1. At this time, the rear end of the lancet 2 is engaged with the concave portion 19a of the connector receiver 19, and the connector receiver 19 moves back as the user continues to push the protection cover 3, and the tapered projection 20a of the driving lever 20 that is fixed to the connector receiver 19 is engaged with the tapered projection 11a that is provided at the ceiling in the measuring device 11 as shown in FIG. 5(b), whereby the connector receiver 19 is locked. In this state, attachment of the lancet-integrated sensor 10 to the measuring device 11 is completed.

Next, a blood collecting operation and a blood dropping operation will be described. When attachment of the lancet-integrated sensor to the measuring device is completed, the vicinity of a semi-circular head portion of the sensor 10 is slightly exposed from the holder 13 as shown in FIG. 3(a). The user holds the measuring device 11, and lightly presses the front end of the sensor 10 against a portion of his/her body from which blood is to be extracted, such as a fingertip.

Figure 10:
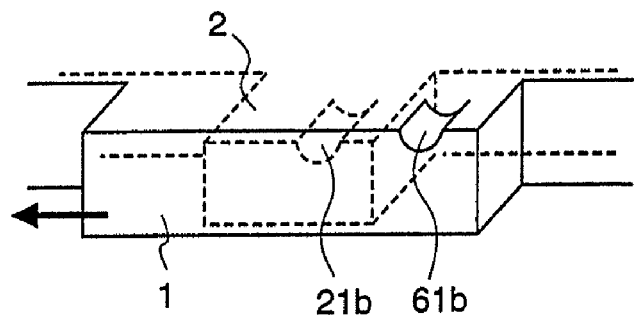
FIG. 10 is a diagram for explaining engagement of a fine concave portion provided in the lancet with a fine convex portion provided in the sensor.

When the user pushes push button (unlocking member) 14, the tapered projection 20a of the driving lever 20 and the tapered projection 11c of the measuring device 11 are disengaged from each other, and the lancet 2 and the sensor 1 are unlocked by extension of the coil spring 18, whereby the lancet 2 is driven (refer to FIG. 10) and, as shown in FIG. 2(c), the needle tip projects from the front end of the sensor 1 to lance skin. At this time, an amount of projection of the needle tip from the sensor is variable by adjustment button 16 shown in FIG. 3(b). To be specific, the torsion spring 21 is moved in a horizontal direction in the measuring device 11 by sliding the adjustment button 16 in the horizontal direction, thereby to adjust a spring force. Alternatively, a distance between the connector receiver 19 that is engaged with the push button 14, and spring stopper 23 is increased or reduced by driving a mechanism (not shown) for converting motion of the adjustment button 16 in the horizontal direction into a to-and-fro motion of the spring stopper 23 along a driving direction of the lancet 2. The amount of projection can be displayed on display unit 12 by converting an amount of sliding of the adjustment button 16 to the amount of projection, with a CPU or the like of the measuring device.

A small amount of blood that is oozing from a lanced fingertip of a patient or a person being tested is dropped onto the front end of the sensor 1, and the blood is drawn into the cavity 5. The measuring device 11 measures blood sugar by an internal electronic circuit, and displays a result of this measurement on the display unit 12. When the result of measurement is displayed to complete measurement, the user operates the slide button (ejection member) 15 to eject the lancet-integrated sensor 10 from the measuring device 11, and this ejected lancet-integrated sensor 10 is disposed of.

At this time, the ejection lever (ejection member) 22 that is united with the slide button 15 pushes the sensor 1 from its rear end. At a beginning of pushing, the connector 2b at the rear end of the lancet 2 is engaged with the concave portion 19a of the connector receiver 19 of the measuring device 11. Therefore, the sensor 1 is ejected before the lancet 2 by operating the slide button 15. Accordingly, a positional relationship between the sensor 1 and the lancet 2 becomes as shown in FIG. 5(b). That is, the fine concave portions 21a and 21b of the lancet 2 are engaged with the fine convex portions 61a and 61b of the concave grooves 60a and 60b of the sensor 1, and the lancet 2 is locked in the state where its needle tip does not project from the sensor 1. When the slide button 14 is further pushed, the lancet 2 with the needle tip 2a being locked in the sensor 1 is ejected together with the sensor 1 from the measuring device 11. Therefore, the needle 2a of the lancet 2 is not exposed from the sensor 1, thereby preventing injury or infectious disease caused by the needle tip being exposed.

As described above, according to the second embodiment of the invention, the lancet-integrated sensor is ejected in a state where the lancet 2 and the sensor 1 are reliably locked with each other. At this time, the lancet 2 and the sensor 1 are locked with the needle 2a of the lancet 2 being housed in the sensor 1. Therefore, when taking the lancet-integrated sensor 10 out of the measuring device, there is no possibility that the user touches the needle 2a of the lancet 2 with his/her finger, or pricks the finger with the needle 2a by mistake, thereby preventing infectious diseases. As a result, a lancet-integrated sensor which can be safely ejected from the measuring device is obtained.

Furthermore, it is possible to obtain a measuring device for a lancet-integrated sensor, which can measure bodily fluid with such a safely-detachable lanced-integrated sensor, and can eject the lancet-integrated sensor with the lancet being locked in a state where the needle of the lancet is housed in the sensor, when measurement is ended.

While in this second embodiment a concave portion is provided on the upper surface of the lancet and a convex portion that is engaged with the concave portion is provided on the sensor 2, the positions where the concave portion and convex portion are provided may be arbitrarily set as long as the lancet and the sensor are locked by engagement of the concave portion with the convex portion after end of measurement, and the needle of the lance is housed in the sensor.

Embodiment 3

According to a third embodiment of the present invention, a holder for guiding a lancet-integrated sensor into a measuring device is detachable from the measuring device to enable cleaning or the like of the holder.

To be specific, when a patient extracts bodily fluid using the measuring device with the lancet-integrated sensor according to the first or second embodiment, the patient must apply his/her finger or upper arm to holder-shaped insertion slot 13 of the measuring device 11 to lance skin, and the bodily fluid of the patient sometimes sticks to the insertion slot 13 of the measuring device 11.

However, since, in the measuring device according to the first or second embodiment, the measuring device 1 is united with the insertion slot 13, the insertion slot 13 cannot be cleaned or replaced after measurement. Therefore, if another patient performs measurement with the measuring device in which another's bodily fluid remains on the insertion slot 13, bodily fluid of the patient might contact the another's bodily fluid, resulting in fear of infectious diseases or the like. Accordingly, the measuring device of the first or second embodiment can be used for personal measurement only.

On the other hand, the measuring device for the lancet-integrated sensor according to the third embodiment enables a user to clean or replace the insertion-slot-shaped holder to which the bodily fluid sticks, whereby the user can handle the measuring device safely and cleanly.

FIGS. 11(a), 11(b) and 12(a)-12(c) are diagrams illustrating construction of the measuring device for the lancet-integrated sensor, according to the third embodiment of the invention.

Figure 11:
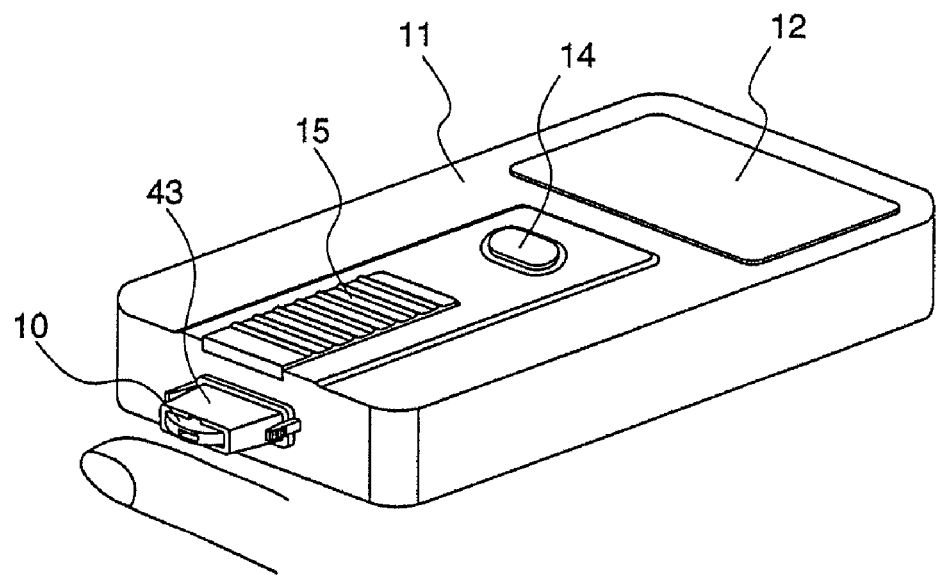
Figure 11:
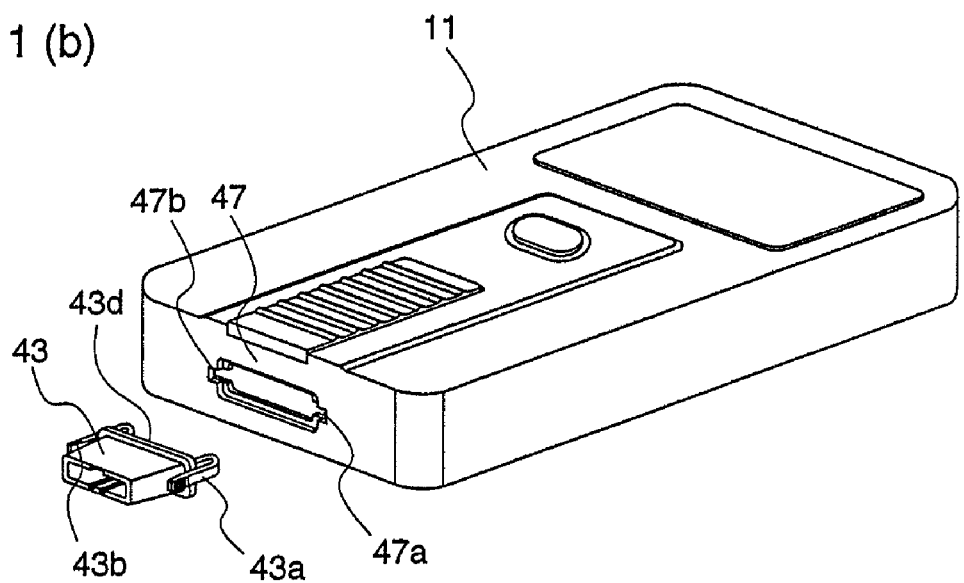

FIG. 11(a) is a perspective view of a lancet-integrated sensor and a measuring device to be combined with the sensor, and FIG. 11(b) shows a state when a holder is disconnected.

In FIGS. 11(a) and 11(b), reference numeral 11 denotes a measuring device for a lancet-integrated sensor (hereinafter referred to as a measuring device) for measuring blood sugar or the like with a lancet-integrated sensor 2 that is fitted thereto, and reference numeral 10 denotes a lancet-integrated sensor.

The measuring device 11 has a holder attachment part 47 on a side wall where the lancet lances skin, and a holder body 43 for holding an end portion of the lancet-integrated sensor 10 in the vicinity of a side where the lancet lances the skin is detachably attached to the holder attachment part 47. Further, the measuring device 11 has an operation button 14 for driving the lancet that is fitted thereto, a display 12 for displaying a measurement result or the like, a slide button 15 for ejecting the lancet-integrated sensor 10 from the measuring device 11, and a holder attachment part 47 to which the holder body 43 is attached.

As shown in FIG. 11(b), the holder body 43 is detachable from the measuring device 11 so that bodily fluid that sticks to the holder body 43 can be washed away or the holder body 43 can be replaced with another one after completion of measurement.

Further, as already described above, the lancet-integrated sensor 10 is constituted by integrating the lancet 2 for lancing the skin of a man or an animal to extract bodily fluid, and the sensor 1 for analyzing this extracted bodily fluid.

Hereinafter, constructions of the holder body 43 and the holder attachment part 47 will be described in more detail, with reference to FIGS. 12(a)-12(c).

Figure 12:
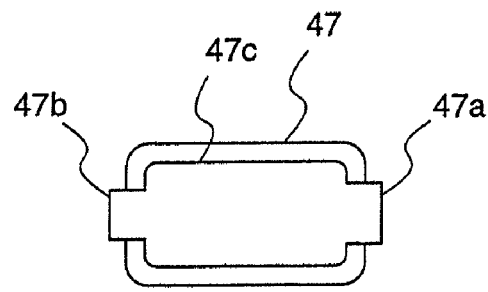
Figure 12:
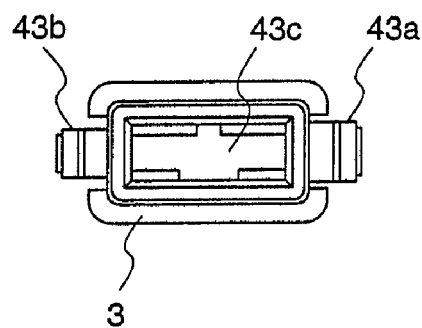
Figure 12:
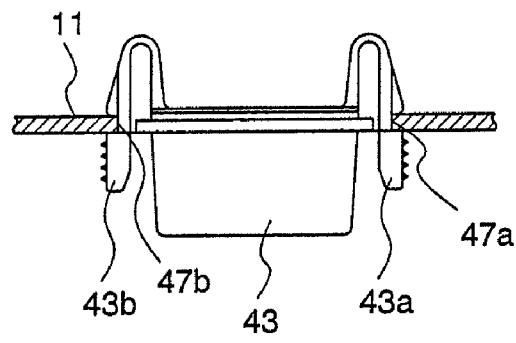
Figure 12:
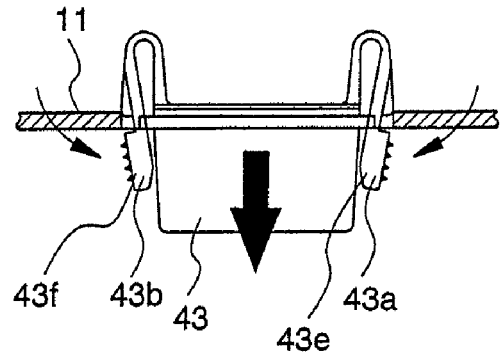

FIGS. 12(a)-12(c) are diagrams for explaining attachment/detachment of the holder body 43 to/from the holder attachment part 47.

With reference to FIG. 12(a), reference numerals 43a and 43b denote hinge-shaped stoppers possessed by the holder body 43. These stoppers are formed by bending plate members, which are extended forward from both ends of the holder body 43, i.e., in a direction opposite to a direction along which the lancet-integrated sensor is inserted, backward at approximately 180°. The stoppers 43a and 43b have, at their front ends, clip parts 43e and 43f which serve as retainers of the stoppers 43a and 43b, and perform positioning when the holder body 43 is stopped at opening 47c, respectively. Inner sides of the hinge-shaped stoppers are fixed onto the holder body 43, and outer sides of the hinge-shaped stoppers are engaged with engagement parts of the holder attachment part 47, whereby the holder body 43 is stopped by connecting it to the measuring device 11. That is, the holder body 43 is stopped, with its spring force, at holes (small openings) 47a and 47b which are formed at two shorter sides of the holder attachment part 47 having an opening shape approximately equal to an outer shape of the holder body 43 so as to increase a width of the holder attachment part 47 to some extent. The holes 47a and 47b may be formed at two longer sides of the opening 47a of the approximately-rectangular holder attachment part 47.

The holder body 43 can be attached to the holder attachment part 47 of the measuring device 11 by inserting the stoppers 43a and 43b of the holder body 43 into the holes 47b and 47b of the holder attachment part 47, respectively. As shown in FIG. 12(a), the holes 47a and 47b of the holder attachment part 47 have different sizes and the stoppers 43a and 43b of the holder body 43 have different sizes, whereby the holder body 43 cannot be inserted upside down. A reason for this is as follows. If the lancet-integrated sensor 10 is inserted upside down into the measuring device 11, electrical connection between the lancet-integrated sensor 10 and the measuring device 11 cannot be made. In order to avoid this problem, right and left holes of the holder attachment part 47 are formed in different shapes and the right and left stoppers of the holder body 43 are also formed in different shapes, so that the holder body 43 can be inserted into the holder attachment part 47 only when its up-to-down direction is a certain direction, i.e., a normal direction, whereby the lancet-integrated sensor 10 cannot be inserted upside down.

FIG. 12(b) and FIG. 12(c) are cross-sectional views in a case where the holder body 43 is stopped by connecting it to the measuring device 11. FIG. 12(b) shows a state where the hinge-shaped stoppers 43a and 43b of the holder body 43 are engaged with the holes 47a and 47b of the measuring device 11. Further, FIG. 12(c) shows a state where a user tries to detach the holder body 43 by pressing the clip portions 43e and 43f of the stoppers 43a and 43b with fingers to replace the holder body 43, after measurement is completed or when another person uses the measuring device 11.

Since the holder for attaching the lancet-integrated sensor, which is possessed by the measuring device, is detachable as described above, the holder body onto which bodily fluid sticks can be replaced with an unused one or washed, whereby the measuring device can be used not only by a specific user but also by anyone other than the user, without fear of infectious diseases or the like. Therefore, the measuring device for the lancet-integrated sensor can be used safely and cleanly.

Further, since the holder body is provided with the hinge-shaped stoppers to be engaged with the holder attachment part, fixation and attachment/detachment of the holder body can easily be performed.

Furthermore, since the holes of the holder attachment part have different shapes and the stoppers of the holder body also have different shapes, the holder body can always be attached in a normal direction to the measuring device, thereby preventing the lancet-integrated sensor from being inserted upside down into the measuring device.

While in this third embodiment shapes of the left and right stoppers 43*a* and 43*b* of the holder body 43 are different from each other and shapes of the left and right holes 47*a* and 47*b* of the holder attachment part 47 are also different from each other, these engagement parts of the holder body and the holder attachment part may have arbitrary shapes as long as respective engagement parts are asymmetrical in a vertical or horizontal direction so that the holder body can be attached to the holder attachment part only when the holder body is inserted in a predetermined direction.

Figure 13:
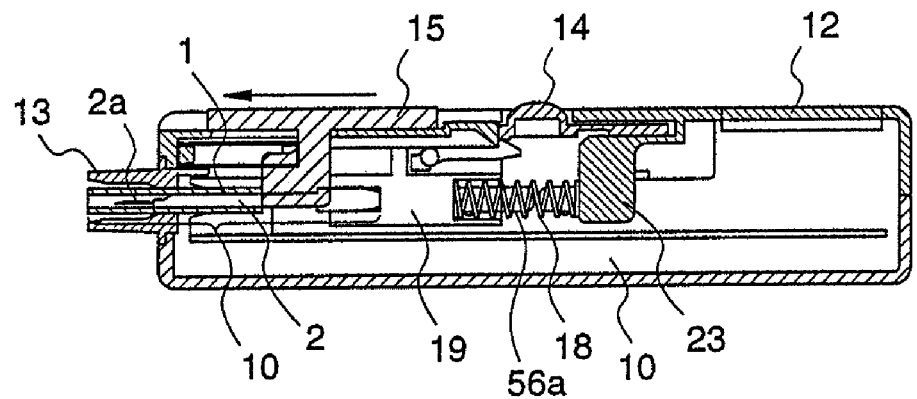
Figure 13:
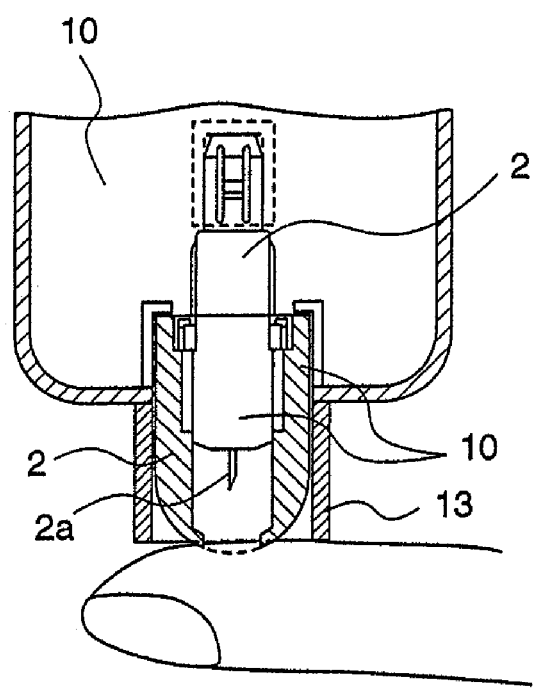

Furthermore, the spring stopper 23 of the measuring device 11 may be fixed to a ceiling of the measuring device 11 as shown in FIG. 13(*a*), and the coil spring 18 may be attached to a shaft 56*a* that is fixed onto the spring stopper 23.

Furthermore, the lancet-integrated sensor 10 may have a shape that is a little shorter in a longitudinal direction as shown in FIG. 13(*b*).

Embodiment 4

According to a fourth embodiment of the present invention, an amount of projection of a needle tip from a lancet-integrated biosensor can be easily adjusted. Further, when the lancet is driven so as to project out forcibly, if drive is stopped halfway due to some trouble, the lancet can easily be returned to a state before being driven.

To be specific, in the measuring device for the lancet-integrated sensor according to the first or second embodiment, when extraction of bodily fluid is performed, the driving member 100 is operated by pushing down the operation button 14 to drive the lancet 2 so that the needle 2*a* lances a fingertip or upper arm, and extracted blood is dropped onto the sensor 1 to perform measurement of the blood. However, when extraction of bodily fluid cannot be performed due to some trouble such as insufficient lancing by the lancet, the lancet 2 must be reset to a state where the lancet 2 can be driven again.

However, in order to reset once driven lancet 2 to the state where it can be driven again, the lancet-integrated sensor 10 must be once ejected by using the slide button 15 and, thereafter, reattached to the measuring device 11. It is sometimes necessary to replace the lancet-integrated sensor 10 itself.

Further, since the lancet-integrated sensor according to the first or second embodiment is not provided with an effective device for adjusting the amount of projection of the needle tip of the lancet, it is difficult to adjust an amount of bodily fluid oozing from a patient or reduce pain of the patient.

On the other hand, the measuring device for the lancet-integrated sensor according to the fourth embodiment can easily adjust the amount of projection of the needle tip of the lancet, and it can perform re-preparation for measurement when bodily fluid cannot be extracted due to some trouble such as insufficient lancing by the lancet.

Hereinafter, a measuring device for the lancet-integrated sensor according to the fourth embodiment will be described.

Figure 14:
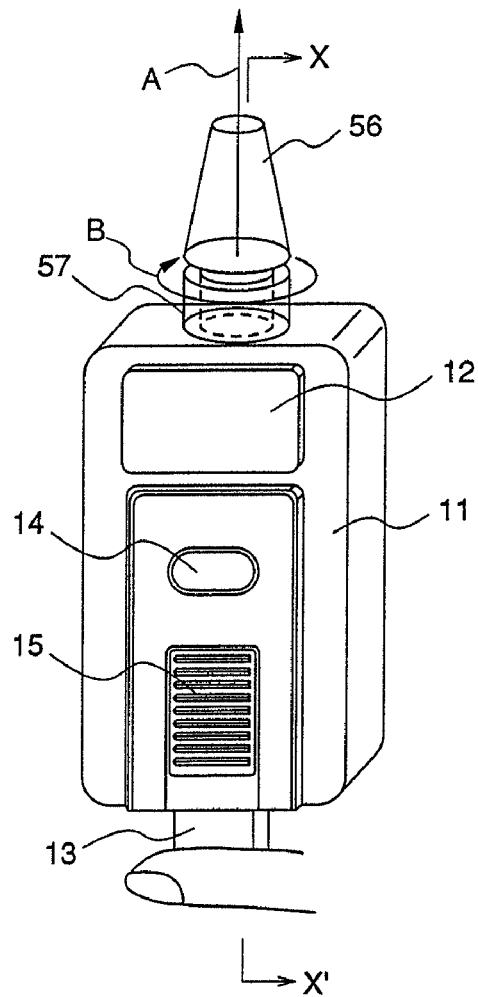
FIG. 14 is a diagram illustrating an appearance of a measuring device which uses a lancet-integrated sensor according to a fourth embodiment of the invention.

FIG. 14 is a diagram illustrating an example of the measuring device according to the fourth embodiment of the present invention.

With reference to FIG. 14, reference numeral 11 denotes a measuring device for a lancet-integrated sensor (hereinafter referred to as a measuring device) according to the fourth embodiment of the invention. Reference numeral 13 denotes an insertion slot into which the lancet-integrated sensor is inserted, and the insertion slot is applied to a finger or upper arm of a patient when measurement is performed; numeral 14 denotes an operation button for driving the lancet that is fitted to the measuring device 11; numeral 12 denotes a display for displaying a result of measurement or the like; numeral 15 denotes a slide button for ejecting the lancet-integrated sensor from the measuring device 11; numeral 56 denotes a pull stick for returning the lancet-integrated sensor back to a stand-by position where measurement can be performed with the lancet-integrated sensor being fitted to the measuring device 11, by pulling the lancet-integrated sensor in a direction opposite to the lancet driving direction, i.e., in a direction shown by arrow A in FIG. 14, when some trouble occurs in extracting bodily fluid; and numeral 57 denotes a lancet projection amount adjuster for adjusting the amount of projection of the needle tip of the lancet, which also serves as a stopper of the pull stick 56.

Figure 15:
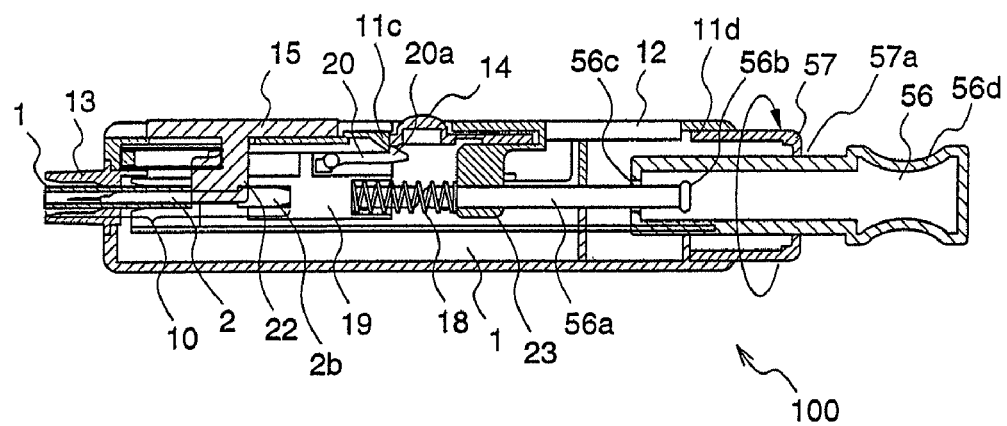
FIG. 15 is a cross-sectional view illustrating an internal structure of the measuring device according to the fourth embodiment of the invention.

FIG. 15 is a cross-sectional view taken along line X-X', of the measuring device for the lancet-integrated sensor shown in FIG. 14. In FIG. 15, the pull stick 56 has a handle part 56*d*. The same constituents as those described with respect to FIG. 14 are given the same reference numerals to omit description thereof.

In FIG. 15, reference numeral 10 denotes a lancet-integrated sensor fitted to the measuring device 11, which is constituted by integrating the lancet 2 for lancing skin of a man or an animal to extract bodily fluid, and sensor 1 for analyzing this extracted bodily fluid.

Further, reference numeral 19 denotes a connector receiver having a concave portion 19*a* that is engaged with a connector 2*b* possessed by the lancet 2 as a component of the lancet-integrated sensor 10. Reference numeral 56*a* denotes a shaft, and the connector receiver 19 for receiving an end of the lancet 2, which end is opposed to a side where the skin is lanced, is fixed to an end of the shaft 56*a*, which end is opposite to the side where the skin is lanced. An end (slip-out prevention member) 56*b* of the shaft 56*a*, which is positioned within the pull stick 56, has a diameter larger than a diameter of an opening 56*c* of the pull stick 56. Reference numeral 20 denotes a driving lever which is provided on the connector receiver 19, and the driving lever 20 stops movement of the connector receiver 19 against a force by which the connector receiver 19 is moved in a direction along which the lancet 2 lances the skin, by spring 18 which is fitted to the shaft 56*a* that is unlocked by pressing the operation button 14 for starting operation of driving member 100. The operation button 14, the pull stick 56, the lancet projection amount adjuster 57, the shaft 56*a*, and the connector receiver 19 constitute the driving member 100 which drives the lancet 2 from its stand-by position along the longitudinal direction of the sensor 1, i.e., the direction along which it lances the skin and, thereafter, returns the lancet back to the stand-by position, with the lancet-integrated sensor 10 being fitted to the measuring device 11.

Next, operation will be described.

First of all, a patient pushes the lancet-integrated sensor 10 into the sensor insertion slot 13 of the measuring device 11, whereby the connector 2*b* possessed by the lancet 2 of the lancet-integrated sensor 10 is engaged with the concave portion 19a of the connector receiver 19, and a tapered projection (claw portion) 20a of the driving lever 20 fixed to the connector receiver 19 is engaged with a tapered projection (claw portion) 11c of the measuring device 11 so that the lancet 2 can be shot by pressing down the operation button 14.

Thereafter, the patient applies the insertion slot 13 of the measuring device 11 to his/her finger or upper arm, and presses the operation button 14, whereby the tapered projection 20a of the connector receiver 19 is disengaged from the tapered projection 11c of the measuring device 11, and the lancet 2 is shot from the tip of the sensor 10.

At this time, if the lancet 2 fails to lance the skin or measurement does not go well due to some trouble, the user picks the pull stick 56 and pulls it in the direction of the arrow shown in FIG. 14, i.e., upward in the Figure, whereby the end 56b of the shaft 56a is pulled up, and the connector receiver 19 holding the connector 2b of the lancet 2 is operated in synchronization with the shaft 56a. Thus, the tapered projection 20a provided on the connector receiver 19 can be re-engaged with the tapered projection 11c just before the operation button 14.

Further, when the lancet 2 is shot, the lancet 2 moves along the longitudinal direction of the sensor 1, and the pull stick 56 that is operated in synchronization with the lancet 1 moves until reaching an opposed surface of the lancet projection amount adjuster 57. The lancet projection amount adjuster 57, which serves as a stopper for the pull stick 56, has a structure of a screw thread to be screwed into a screw hole 11d that is formed on a side of the measuring device 11 opposite to the insertion slot 13. The lancet projection amount adjuster 57 can be moved along a lancet moving direction by rotating it clockwise or counterclockwise.

Therefore, the measuring device 11 adjusts a position of the lancet projection amount adjuster 57 in advance of driving the lancet 2, and adjusts a spring force by adjusting a distance between the connector receiver 19 and the spring stopper (supporting member) 23, thereby setting the amount of projection of the needle 2a of the lancet 2 to a desired amount. Thus, shot lancet 2 moves until the pull stick 56 hits the lancet projection amount adjuster 57 to stop, whereby the amount of projection of the needle tip of the lancet 2 from the sensor can be adjusted.

As described above, according to the fourth embodiment, even when the lancet 2 fails to lance the skin or measurement does not go well due to some trouble, preparation for re-measurement can be easily performed using the pull stick 56 which sets the connector receiver 19 holding the connector 2b of the lancet 2, beneath the operation button 14 again to bring the measuring device into a state where measurement can be performed.

Furthermore, since the measuring device 11 is provided with the lancet projection amount adjuster which can adjust the amount of projection of the lancet, an amount of bodily fluid oozing from a patient can be adjusted, or pain of the patient can be reduced.

Embodiment 5

A fifth embodiment according to the present invention provides a biosensor cartridge, by which a biosensor or a lancet-integrated sensor can be fitted to a measuring device without a troublesome operation.

Hereinafter, a biosensor cartridge according to the fifth embodiment of the invention will be described taking, as an example, a cartridge which houses biosensors for electrochemically measuring blood sugar, with reference to the drawings.

Figure 16:
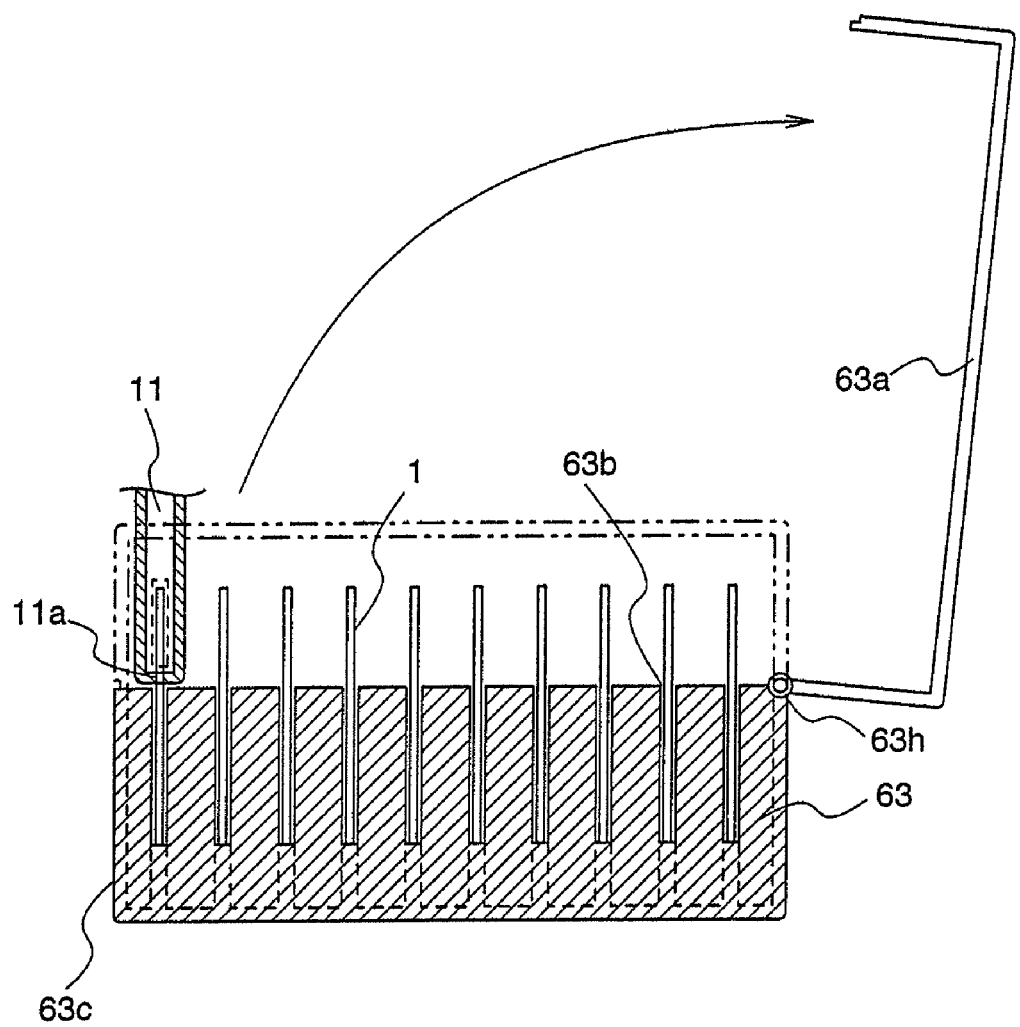
FIG. 16 is a cross-sectional view illustrating a biosensor cartridge according to a fifth embodiment of the invention.

FIG. 16 is a diagram illustrating a biosensor cartridge according to the fifth embodiment of the invention.

In FIG. 16, reference numeral 1 denotes biosensors for measuring blood sugar, and each biosensor 1 is formed of a plate member that is approximately rectangular in shape, and one of two shorter sides of rectangular biosensor 1 is semi-circular in shape. Reference numeral 11 denotes a measuring device for measuring blood sugar with the biosensor 1 attached thereto. Reference numeral 63 denotes a biosensor cartridge comprising plastic or the like, and the cartridge 63 has an approximately-rectangular-parallelepiped housing box (cartridge body) 63c, and plural housing sections 63b which are slits each conforming to the shape of the biosensor 1. The housing sections 63b can hold plural biosensors 1 separately, by perpendicularly supporting the biosensors 1 with their end portions to be inserted into the measuring device 11 facing up. A spacing between the housing sections (slits) 63b for housing the biosensors 1 should be sufficiently large so that insertion slot 11a of the measuring device 11 can be pressed onto each of these separately housed biosensors 1. That is, when inserting a target biosensor 1 into the insertion slot 11a of the measuring device 11, this spacing prevents the insertion slot 11a from contacting biosensors adjacent to a target biosensor. Reference numeral 63a denotes a lid (lid part) of the biosensor cartridge 63. The lid 63a is hollow and approximately rectangular-parallelepiped in shape, and the lid 63a is opened or closed by rotating it about 90 degrees about a hinge 63h that is provided on a side of the housing box 63c.

Figure 17:
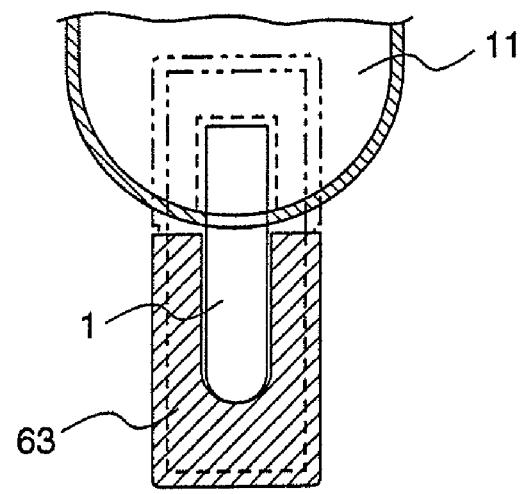
Figure 17:
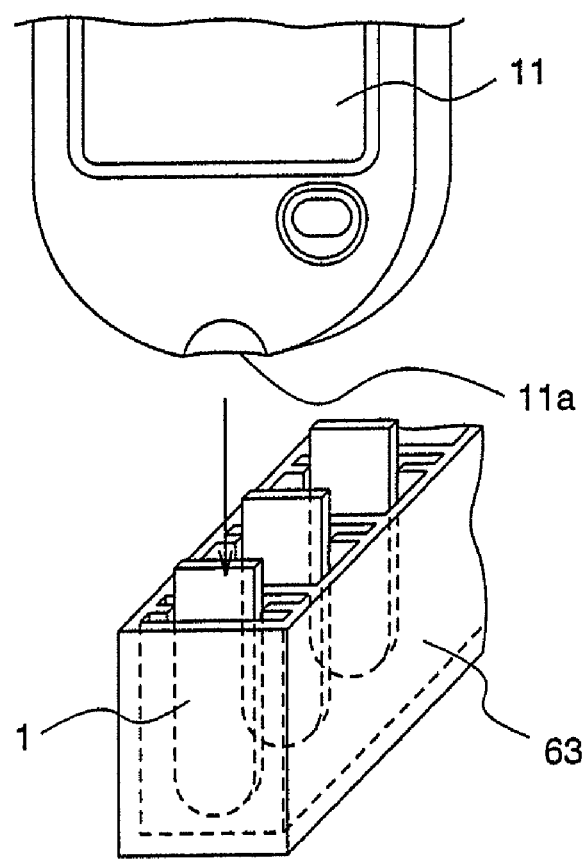

FIGS. 17(a) and 17(b) are diagrams illustrating a state where one of the biosensors housed in the biosensor cartridge of the fifth embodiment is inserted into the measuring device.

Attachment of the biosensor 1 to the measuring device 11 is performed as follows. After the lid 63a of the biosensor cartridge 63 is opened as shown in FIG. 16, the biosensor 1, which is stored in the biosensor cartridge 63 with its semi-circular end facing up, is inserted into the biosensor insertion slot 11a of the measuring device 11 as shown in FIGS. 17(a) and 17(b).

At this time, the spacing between the housing sections 63b for housing the biosensors 1 is set so that, when a target biosensor 1 is inserted into the insertion slot 11a of the measuring device 11, the insertion slot 11a does not contact the biosensors adjacent to the target biosensor. Therefore, the target biosensor 1 can be easily attached to the measuring device 11 without damaging other biosensors 1.

As described above, according to the biosensor cartridge of the fifth embodiment, the spacing between respective housing sections provided in the biosensor cartridge is sufficiently large so that one of separately stored biosensors 1 can be inserted into the insertion slot 11a of the measuring device 11. Therefore, the biosensor 1 can be inserted into the measuring device 11 with a single touch, whereby preparation for measurement can be easily performed. Consequently, each of the biosensors stored in the cartridge can be inserted into the measuring device 11 without a troublesome operation, and it is possible to minimize such accident that the insertion slot 11a of the measuring device contacts the biosensors adjacent to the target biosensor thereby to damage the biosensors.

Modification 1 of Embodiment 5

Hereinafter, a biosensor cartridge according to a first modification of the fifth embodiment will be described. The biosensor cartridge according to this first modification is characterized in a manner of hermetically sealing the cartridge. Since other constituents are identical to those described for the fifth embodiment, the same reference numerals are given to the constituents to omit description thereof.

Figure 18:
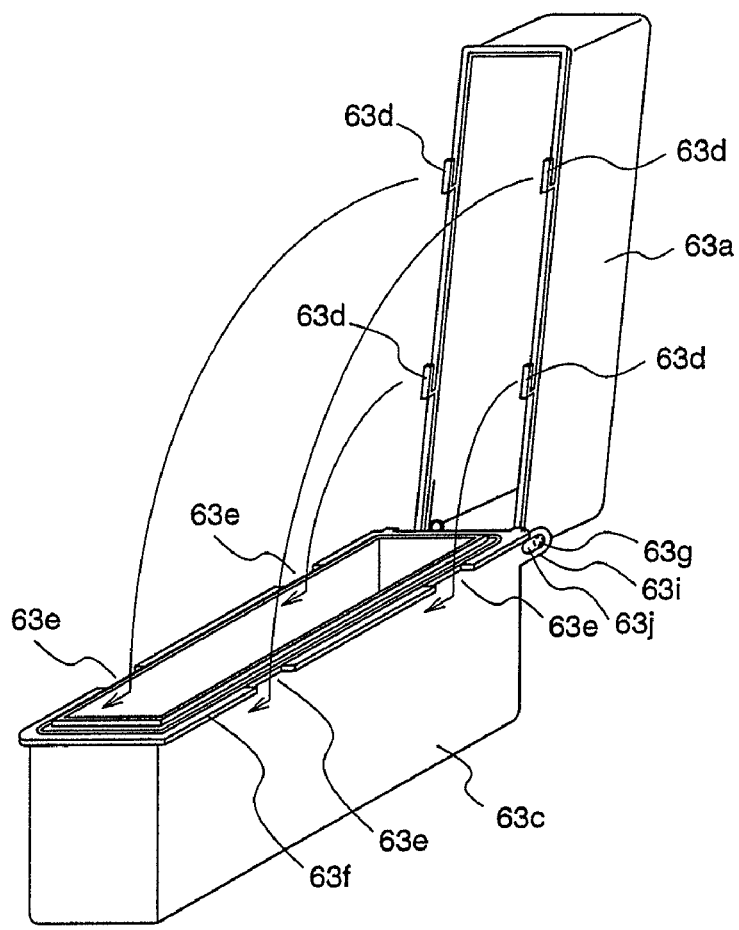
Figure 18:
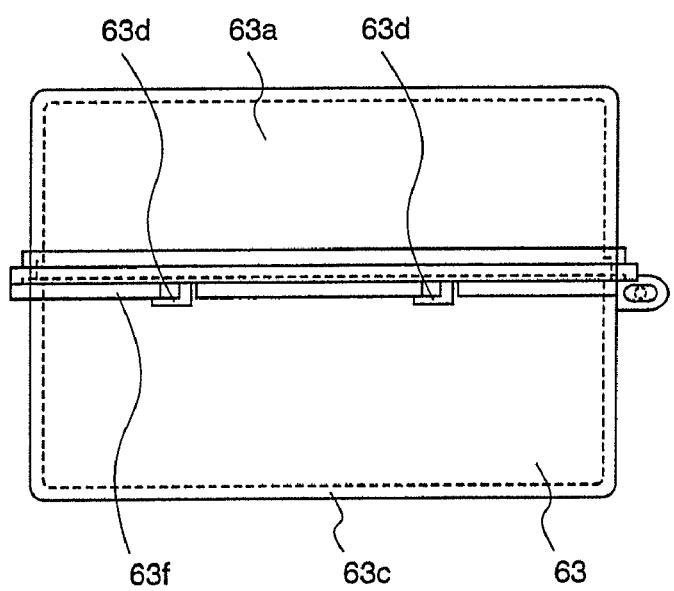
Figure 18:
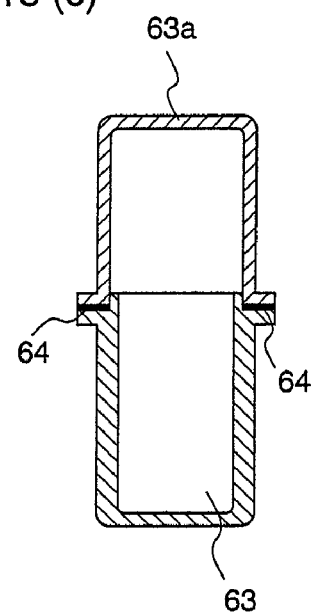

FIGS. 18(a)-18(c) are diagrams illustrating a biosensor cartridge according to the first modification of the fifth embodiment.

As shown in FIG. 18(a), in the biosensor cartridge 63, an approximately-rectangular-parallelepiped lid 63a having a hollow inside is rotatably fixed onto an approximately-rectangular-parallelepiped housing box 63c with a hinge whose rotational axis is slidable in a longitudinal direction of the lid 63a.

The hinge is composed of a pair of axial projections 63g which project in a vertical direction with respect to side surfaces forming longer sides of the lid 63a from vicinities of both ends of a shorter side of the opening of the lid 63a; a side-to-side-long bearing 63i which extends within the same plane as side surfaces along the longer sides of the opening of the housing box 63c from vicinities of the both ends of the shorter side of the opening; and a bearing hole 63, which is formed in the bearing 63i in an oval shape, with which the axial projections 63g are engaged.

Then, four reverse-L-shaped projections 63d which are formed at edges of respective sides of the opening of the lid 63a are positioned at four notches 63e formed in a projection part (peripheral edge part) 63f which is formed at edges of respective sides of an upper surface of the housing box 63c of the biosensor cartridge 63, and the projections 63d are received within the notches 63e. Then, the lid 63a is rotated by 90° in a direction indicated by an arrow (i.e., counterclockwise) and, thereafter, slightly slid in a radial direction (i.e., left forward direction in FIG. 18(a)), whereby the L-shaped projections 63d are engaged with the projection part 63f in the vicinity of the notches 63e, and the lid 63a seals the housing box 63c having the plural housing slits, of the biosensor cartridge 63. FIG. 18(b) is a side view illustrating a state where the housing box is sealed with the lid, from a state shown in FIG. 18(a).

Further, FIG. 18(c) is a cross-sectional view illustrating a state where an elastic member (sealing member) 64 is disposed on a part where the housing box 63c and the lid 63a closely contact each other (i.e., on a peripheral edge part of the opening of the lid 63a) to hermetically seal the container. The elastic member 64 is a member having large elasticity such as rubber. In this way, hermeticity of the biosensor cartridge can be increased by integrally forming the elastic member 64.

Although the shape of the biosensor housing part is not particularly described above, plural slits, each conforming to the shape of the biosensor, may be formed at regular intervals in a member that fills a concave portion of the approximately-rectangular-parallelepiped housing box 63c. Thereby, the biosensors can be perpendicularly supported at regular intervals so that, when inserting the target biosensor 1 into the insertion slot 2a of the measuring device 2 as in the fifth embodiment, the insertion slot 2a does not contact adjacent biosensors.

As described above, according to the first modification of the fifth embodiment, the elastic member 64 or the like is formed integrally with the engagement part of the housing box 63c and the lid 63a of the biosensor cartridge 63, and the housing box 63c is covered with the lid 63a. Thereafter, the L-shaped projections 63d provided on the lid 63a are received within the notches 63e of the projection part 63f of the biosensor cartridge, and the L-shaped projections 63d are slid to be engaged with the notches 63e, thereby hermetically sealing the container. Therefore, the hermeticity of the container is increased, and moisture in the container is reduced, whereby the sensor is prevented from being contaminated by the moisture, leading to improvement in accuracy of the sensor.

Modification 2 of Embodiment 5

Figure 19:
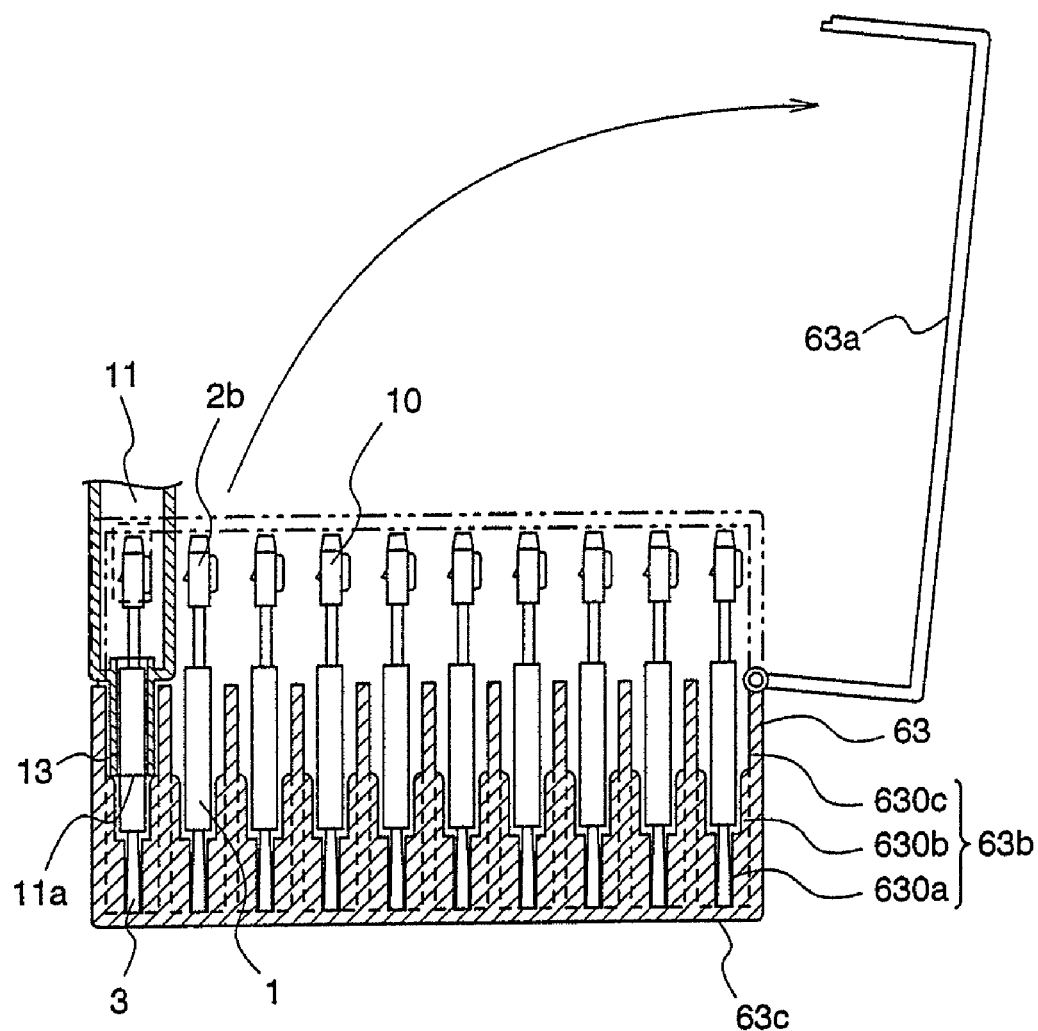
FIG. 19 is a diagram illustrating a biosensor cartridge according to a second modification of the fifth embodiment of the invention.

FIG. 19 is a diagram illustrating a biosensor cartridge according to a second modification of the fifth embodiment of the present invention.

In FIG. 19, reference numeral 10 denotes a lancet-integrated sensor which is constituted by integrating a lancet for lancing skin of a man or an animal to extract bodily fluid, and a sensor for analyzing extracted bodily fluid; reference numeral 11 denotes a measuring device for measuring blood sugar or the like with a lancet-integrated sensor 5 that is attached thereto; and reference numeral 63 denotes a biosensor cartridge comprising plastic or the like, which is composed of an approximately-rectangular-parallelepiped lid 63a and an approximately-rectangular-parallelepiped housing box 63c. The housing box 63c is provided with lower grooves 630a, intermediate grooves 630b, and upper grooves 630c so as to support the lancet-integrated sensors 10, each having a protection cover (protector) 3 on its bottom surface, perpendicularly at regular intervals. To be specific, the lower grooves 630a, into which protection covers 3 of the lancet-integrated sensors 10 are inserted to be supported, are formed at a side nearest to a bottom of a member that fills up a concave portion of the housing box 63c. The intermediate grooves 630b, into which portions of the lancet-integrated sensors 10 are inserted to be supported, are formed above the lower grooves. The upper grooves 630c are formed above the intermediate grooves, and lowermost portions of the upper grooves 630c are a little rounded to increase widths of these grooves, and approximately entire portions thereof are wider than widths of the sensors of the lancet-integrated sensors 10. A single housing part (groove) 63b is formed of a lower groove (first groove) 630a, an intermediate groove (second groove) 630b, and an upper groove (third groove) 630c which are connected with each other. In the housing box 63a, the lancet-integrated sensors 10 are respectively housed in the plural housing parts 63b at regular intervals, with portions to be inserted to the measuring device 11 facing upwardly.

A spacing between the housing parts for housing the lancet-integrated sensors should be sufficiently large so that the insertion slot 11a of the measuring device 11 can be pressed onto each of separately stored lancet-integrated sensors 10. As an example of the lancet-integrated sensor, the lancet-integrated sensor which has already been described for the first or second embodiment may be employed.

Figure 20:
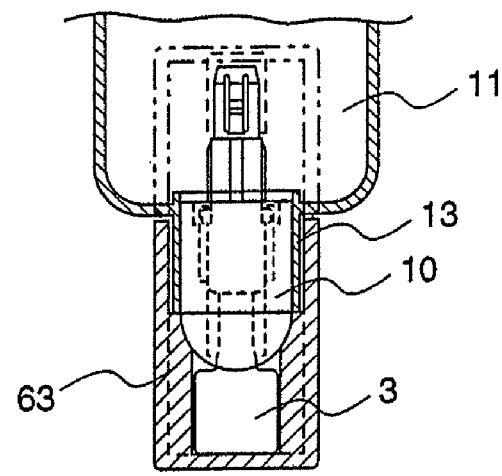
Figure 20:
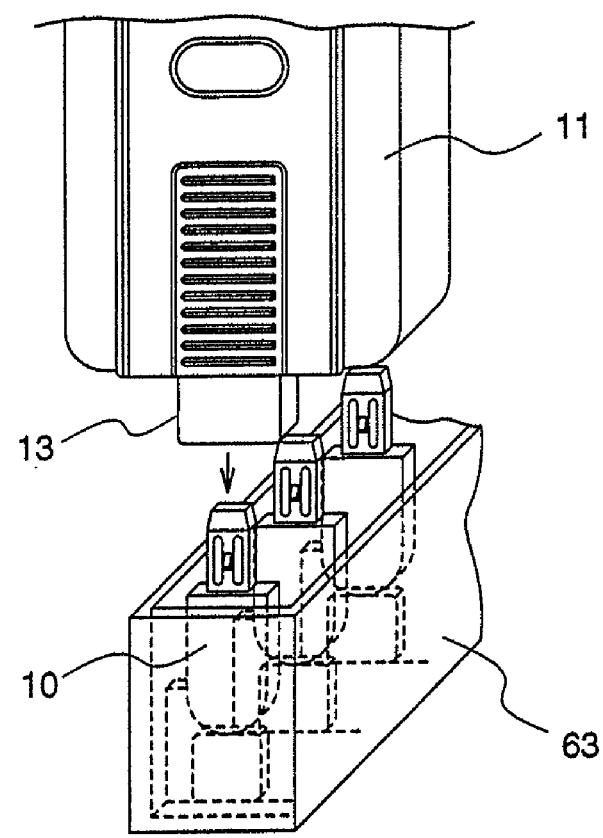
Figure 21:
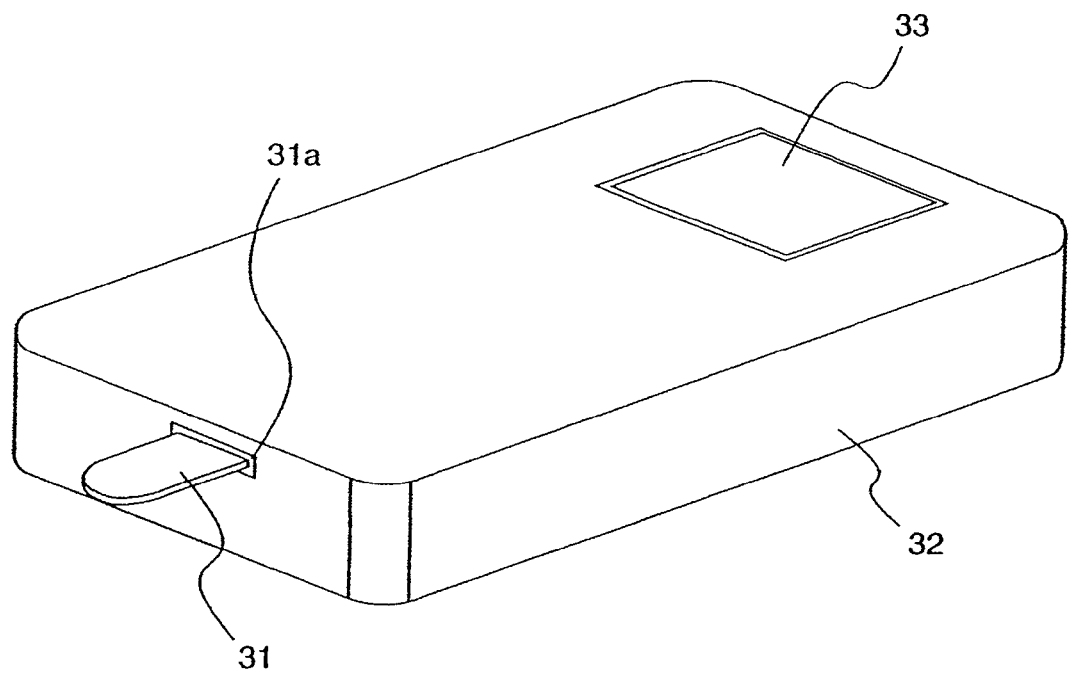
FIG. 21 is a perspective view illustrating an example of a conventional measuring device for a biosensor.
Figure 22:
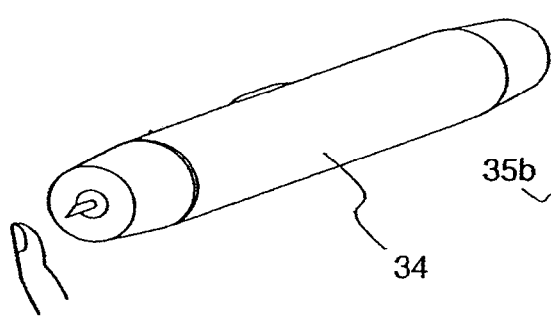
Figure 22:
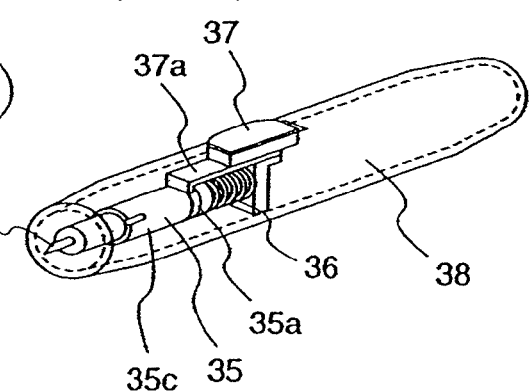

FIG. 20(a) is a constitutional diagram for explaining attachment of a lancet-integrated sensor to a measuring device, and FIG. 20(b) is a perspective view thereof.

FIG. 20(a) shows a lancet-integrated sensor having a needle storage part that is a little wider than those shown in FIG. 1 and other figures.

Attachment of the lancet-integrated sensor 10 to the measuring device 11 is performed as follows. After the lid 63a of the biosensor cartridge 63 is opened as shown in FIG. 19, the lancet-integrated sensor insertion slot 11a of the measuring device 11 is pressed onto the lancet-integrated sensor 1 that is stored in biosensor cartridge 63 as shown in FIG. 20(b).

As described above, according to the fifth embodiment, a spacing between respective storage parts of the biosensor cartridge is sufficiently large so that the insertion slot 11a of the measuring device 11 can be pressed onto one of the lancet-integrated sensors 10 that are stored separately, whereby the lancet-integrated sensor 10 can be inserted into the measuring device 11 by a single touch, and preparation for measurement can be easily performed as compared with a measuring device for the sensor having no lancet. Therefore, each of the biosensors stored in the housing case can be inserted into the measuring device 11 without performing a troublesome operation, and the insertion slot 11a of the measuring device 11 is prevented from contacting the biosensors adjacent to the target biosensor, to thereby prevent damage to the biosensors.

Although the biosensors are perpendicularly supported in the first or second modification of the fifth embodiment, when a height of the biosensor cartridge should be reduced, the biosensors may be supported in a slanting direction. Also in this case, the same effects as mentioned above are achieved by providing biosensor storage parts at regular intervals with which the insertion slot of the measuring device can be pressed onto a target biosensor without damaging adjacent biosensors.

APPLICABILITY IN INDUSTRY

As described above, according to a lancet-integrated sensor of the present invention and a measuring device to be combined with the sensor, a sensor and a lancet are integrated, and a measuring device for measuring characteristics of bodily fluid is provided with a function of driving the lancet. Therefore, as compared with a conventional system comprising a sensor, a lancet, a measuring device, and a lancet device, a number of components is reduced, whereby management is facilitated. Especially, it is not necessary to manage a number of disposal sensors and lancets separately. Further, when carrying these devices, volume is reduced, resulting in convenience of portability.

Further, when preparing for measurement, it is not necessary to set a sensor on a measuring device and a lancet on a lancet device, respectively, as is conventional, and preparation for measurement can be completed by only a single operation of setting a lancet-integrated sensor onto a measuring device. Further, trouble associated with replacing a used sensor with a new one is reduced by half.

Furthermore, since a lancet is locked with its needle tip being housed in a sensor, an accident due to careless exposure of the needle tip is avoided.

Moreover, since a cartridge for housing plural sensors can support sensors at regular intervals, it is possible to avoid such an accident that, when a sensor is attached to a measuring device, the measuring device damages other sensors.

The invention claimed is:

1. A measuring device for performing measurement of characteristics of a bodily fluid using a lancet-integrated sensor that is detachably attached to said measuring device and that is formed by integrating a lancet for lancing skin to collect the bodily fluid and a sensor for analyzing the collected bodily fluid, the lancet-integrated sensor having a protection cover which includes a grip part, said measuring device including:
    a terminal member arranged to electrically connect with a body of the sensor; and
    a lancet driving mechanism that engages a portion of the lancet, said lancet driving mechanism including an elastic member and a latch;
    wherein said elastic member is provided and arranged to be compressed to store driving power by attaching the lancet-integrated sensor to said measuring device to connect the body of the sensor with said terminal member and to engage the portion of the lancet with said lancet driving mechanism,
    wherein said latch releasably holds said elastic member in a compressed state, and said latch is arranged such that a lancing operation is performed by release of said latch to drive the lancet, and
    wherein said lancet driving mechanism is structured such that said elastic member is compressed during attachment of the lancet-integrated sensor to said measuring device by pushing the grip part of the protection cover toward the measuring device.

2. The measuring device of claim 1, wherein one end of the lancet-integrated sensor projects from said measuring device when attachment of the lancet-integrated sensor to said measuring device is completed.

3. The measuring device of claim 2, wherein said lancet driving mechanism is structured and arranged such that a needle tip of the lancet projects from the body of the sensor only during a lancing operation to lance the skin, and at all other times is housed in the sensor.

4. The measuring device of claim 3, wherein said lancet driving mechanism is structured and arranged to drive the lancet with an end of the lancet that is opposite to a needle tip of the lancet engaged with said lancet driving mechanism.

5. The measuring device of claim 4, wherein said elastic member comprises a spring arranged to apply a force to the lancet in a longitudinal direction of the sensor and said latch is released to release the driving power of said spring by a press button.

6. The measuring device of claim 2, wherein said lancet driving mechanism is structured and arranged to drive the lancet with an end of the lancet that is opposite to a needle tip of the lancet engaged with said lancet driving mechanism.

7. The measuring device of claim 6, wherein said elastic member comprises a spring arranged to apply a force to the lancet in a longitudinal direction of the sensor and said latch is released to release the driving power of said spring by a press button.

8. The measuring device of claim 1, wherein said lancet driving mechanism is structured and arranged such that a needle tip of the lancet projects from the body of the sensor only during a lancing operation to lance the skin, and at all other times is housed in the sensor.

9. The measuring device of claim 8, wherein said terminal member (a) comprises a connection terminal positioned to maintain an electrical connection with an electrode terminal on an end of the body of the sensor and (b) is connected to an internal electric circuit to measure the characteristics of the collected bodily fluid.

10. The measuring device of claim 9, wherein said lancet driving mechanism is structured and arranged to drive the lancet with an end of the lancet that is opposite to a needle tip of the lancet engaged with said lancet driving mechanism.

11. The measuring device of claim 8, wherein said lancet driving mechanism is structured and arranged to drive the lancet with an end of the lancet that is opposite to a needle tip of the lancet engaged with said lancet driving mechanism.

12. The measuring device of claim 11, wherein said elastic member comprises a spring arranged to apply a force to the lancet in a longitudinal direction of the sensor and said latch is released to release the driving power of said spring by a press button.

13. The measuring device of claim 1, wherein said elastic member comprises a spring arranged to apply a force to the lancet in a longitudinal direction of the sensor and said latch is released to release the driving power of said spring by a press button.

14. The measuring device of claim 1, wherein the body of the sensor has a shape of a long and narrow strip and a detachable protection cover fitted to a needle tip of the lancet, the cover being attached during attachment of the lancet-integrated sensor to said measuring device and removed during the lancing operation, and said lancet driving mechanism supports an end of the lancet that is opposite to the needle tip of the lancet.

15. The measuring device of claim 1, wherein a holder is provided to cover a periphery of the lancet to hold the body of the sensor and the lancet so that when the body of the sensor and the lancet are attached to said measuring device, both the body of the sensor and the lancet are held by said holder with an end of the lancet opposite to a needle tip of the lancet being held by said lancet driving mechanism.

16. The measuring device of claim 1, further comprising an operating button operable to eject a used lancet-integrated sensor from said measuring device without an operator touching the lancet-integrating sensor.

17. The measuring device of claim 1, further comprising a display on a body of said measuring device that displays an amount of projection of a needle tip of the lancet from a front end of the sensor.

18. A measuring device for performing measurement of characteristics of a bodily fluid using a lancet-integrated sensor that is detachably attached to said measuring device and that is formed by integrating a lancet for lancing skin to collect the bodily fluid and a sensor for analyzing the collected bodily fluid, the lancet-integrated sensor having a protection cover which includes a grip part, said measuring device comprising:
    a case having an insertion slot for inserting the lancet-integrated sensor into said case;
    a terminal member arranged in said case to electrically connect with a body of the sensor; and
    a lancet driving mechanism for engaging a portion of the lancet, said lancet driving mechanism including a connector receiver arranged in said case, an elastic member attached to said connector receiver, and a latch for holding said connector receiver;
    wherein said elastic member is provided and arranged to be compressed to store driving power by inserting the lancet-integrated sensor through said insertion slot and attaching the lancet-integrated sensor to said measuring device such that the body of the sensor is connected with said terminal member and the portion of the lancet is engaged with said lancet driving mechanism,
    wherein said latch releasably holds said connector receiver to maintain said elastic member in a compressed state, and said latch is arranged such that a lancing operation is performed by release of said latch to drive the lancet, and
    wherein said lancet driving mechanism is structured such that said elastic member is compressed during attachment of the lancet-integrated sensor to said measuring device by pushing the grip part of the protection cover toward said lancet driving mechanism such that the lancet pushes against the connector receiver.

19. A measuring device for performing measurement of characteristics of a bodily fluid, said measuring device comprising:
    a lancet-integrated sensor that is formed by integrating a lancet for lancing skin to collect the bodily fluid and a sensor for analyzing the collected bodily fluid, said lancet-integrated sensor having a protection cover which includes a grip part,
    a case having an insertion slot for inserting said lancet-integrated sensor into said case;
    a terminal member arranged in said case to electrically connect with a body of said sensor; and
    a lancet driving mechanism for engaging a portion of said lancet, said lancet driving mechanism including a connector receiver arranged in said case, an elastic member attached to said connector receiver, and a latch for holding said connector receiver;
    wherein said elastic member is provided and arranged to be compressed to store driving power by inserting said lancet-integrated sensor through said insertion slot and attaching said lancet-integrated sensor to said measuring device such that said body of said sensor is connected with said terminal member and said portion of said lancet is engaged with said lancet driving mechanism,
    wherein said latch releasably holds said connector receiver to maintain said elastic member in a compressed state, and said latch is arranged such that a lancing operation is performed by release of said latch to drive said lancet, and
    wherein said lancet driving mechanism is structured such that said elastic member is compressed during attachment of said lancet-integrated sensor to said measuring device by pushing said grip part of said protection cover toward said lancet driving mechanism such that said lancet pushes against said connector receiver.

* * * * *